(12) United States Patent
Webster et al.

(10) Patent No.: US 7,211,184 B2
(45) Date of Patent: May 1, 2007

(54) CAPILLARY ELECTROPHORESIS DEVICES

(75) Inventors: James Russell Webster, Hsinchu (TW); Yuan-Fong Kuo, Hsinchu (TW); Shao-Tsu Wang, Taipei (TW); Chun-Hsien Lee, Kaohsiung (TW)

(73) Assignee: AST Management Inc., Apia (WS)

( * ) Notice: Subject to any disclaimer, the term of this patent is extended or adjusted under 35 U.S.C. 154(b) by 317 days.

(21) Appl. No.: 10/911,455

(22) Filed: Aug. 4, 2004

(65) Prior Publication Data

US 2006/0027458 A1 Feb. 9, 2006

(51) Int. Cl.
*G01N 27/453* (2006.01)

(52) U.S. Cl. .............. 204/601; 204/451; 204/453; 204/604; 422/100; 422/101

(58) Field of Classification Search .............. 204/604, 204/451, 602–605, 452–455; 422/99–102
See application file for complete search history.

(56) References Cited

U.S. PATENT DOCUMENTS

| 5,296,114 | A | 3/1994 | Manz |
| 5,534,123 | A | 7/1996 | Bashkin et al. |
| 5,569,364 | A | 10/1996 | Hooper et al. |
| 5,599,432 | A | 2/1997 | Manz et al. |
| 5,728,282 | A | 3/1998 | Bashkin et al. |
| 5,741,639 | A | 4/1998 | Ensing et al. |
| 5,750,015 | A | 5/1998 | Soane et al. |
| 5,770,029 | A | 6/1998 | Nelson et al. |
| 5,800,690 | A | 9/1998 | Chow et al. |
| 5,876,675 | A | 3/1999 | Kennedy |
| 5,885,432 | A | 3/1999 | Hooper et al. |
| 5,948,227 | A | 9/1999 | Dubrow |
| 5,964,995 | A | 10/1999 | Nikiforov et al. |
| 5,965,001 | A | 10/1999 | Chow et al. |
| 5,965,237 | A | 10/1999 | Bruin et al. |
| 5,965,410 | A | 10/1999 | Chow et al. |
| 5,976,336 | A | 11/1999 | Dubrow et al. |
| 6,001,229 | A | 12/1999 | Ramsey |
| 6,007,690 | A | 12/1999 | Nelson et al. |
| 6,010,607 | A | 1/2000 | Ramsey |
| 6,010,608 | A | 1/2000 | Ramsey |
| 6,033,546 | A | 3/2000 | Ramsey |
| 6,042,709 | A | 3/2000 | Parce et al. |
| 6,045,676 | A | 4/2000 | Mathies et al. |
| 6,048,498 | A | 4/2000 | Kennedy |

(Continued)

OTHER PUBLICATIONS

Ashton, R., et al., "Microfluidic separation of DNA," Current Opinion in Biotechnology, 14, pp. 497-504 (2003).

(Continued)

*Primary Examiner*—Nam Nguyen
*Assistant Examiner*—V. Surekha
(74) *Attorney, Agent, or Firm*—Jones Day; Brett Lovejoy

(57) ABSTRACT

A capillary electrophoresis device as well as a process for fabrication of the device is disclosed. The capillary electrophoresis device comprises a device body structure having a plurality of reservoirs arrayed thereon for loading a sample, and a plurality of rows of grooves transversely defined to be connected with the reservoirs for receiving at least a capillary electrophoresis chip. The capillary electrophoresis chip comprises a straight main separation channel, an injection channel, and a plurality of sample transport channels defined thereon in liquid communication with the reservoirs. After an electrode means is applied, the sample can be transported into the separation channel for detection and analysis.

12 Claims, 20 Drawing Sheets

U.S. PATENT DOCUMENTS

| | | | |
|---|---|---|---|
| 6,054,034 | A | 4/2000 | Soane et al. |
| 6,056,860 | A | 5/2000 | Amigo et al. |
| 6,068,752 | A | 5/2000 | Dubrow et al. |
| 6,074,827 | A | 6/2000 | Nelson et al. |
| 6,086,740 | A | 7/2000 | Kennedy |
| 6,093,296 | A | 7/2000 | Soane et al. |
| 6,100,535 | A | 8/2000 | Mathies et al. |
| 6,103,199 | A | 8/2000 | Bjornson et al. |
| 6,103,537 | A | 8/2000 | Ullman et al. |
| 6,143,152 | A | 11/2000 | Simpson et al. |
| 6,153,073 | A | 11/2000 | Dubrow et al. |
| 6,156,181 | A | 12/2000 | Parce et al. |
| 6,174,675 | B1 | 1/2001 | Chow et al. |
| 6,176,962 | B1 | 1/2001 | Soane et al. |
| 6,235,175 | B1 | 5/2001 | Dubrow et al. |
| 6,261,431 | B1 | 7/2001 | Mathies et al. |
| 6,270,644 | B1 | 8/2001 | Mathies et al. |
| 6,274,089 | B1 | 8/2001 | Chow et al. |
| 6,280,589 | B1 | 8/2001 | Manz et al. |
| 6,284,113 | B1 | 9/2001 | Bjornson et al. |
| 6,306,272 | B1 | 10/2001 | Soane et al. |
| 6,306,273 | B1 | 10/2001 | Wainright et al. |
| 6,337,740 | B1 | 1/2002 | Parce |
| 6,342,142 | B1 | 1/2002 | Ramsey |
| 6,344,326 | B1 | 2/2002 | Nelson et al. |
| 6,361,671 | B1 | 3/2002 | Mathies et al. |
| 6,406,893 | B1 | 6/2002 | Knapp et al. |
| 6,409,900 | B1 | 6/2002 | Parce et al. |
| 6,423,198 | B1 | 7/2002 | Manz et al. |
| 6,432,290 | B1 | 8/2002 | Harrison et al. |
| 6,440,284 | B1 | 8/2002 | Dubrow |
| 6,444,461 | B1 | 9/2002 | Knapp et al. |

OTHER PUBLICATIONS

Belenky, A., et al., "Sequencing of antisense DNA analogues by capillary gel electrophoresis with laser-induced fluorescence detection," Journal of Chromatography A, 700, pp. 137-149 (1995).

Chan, Y. C., et al., "Design and fabrication of an integrated microsystem for microcapillary electrophoresis," Journal of Micromechanics and Microengineering, 13, pp. 914-921 (2003).

Ehrlich, D. J., et al., "Microfluidic devices for DNA analysis," Tibtech (Trends in Biotechnology), Aug. 1999, 17, pp. 315-319 (1999).

Gawron, A. J., et al., "Microchip electrophoretic separation systems for biomedical and pharmaceutical analysis," European Journal of Pharmaceutical Sciences, 14, pp. 1-12 (2001).

Kopp, M. U., et al., "Developments in technology and applications of microsystems," Current Opinion in Chemical Biology 1997, 1, pp. 410-419 (1997).

Lin, Y.-W., et al., "Analysis of double-stranded DNA by microchip capillary electrophoresis using polymer solutions containing gold nanoparticles," Journal of Chromatography A, 1014, pp. 47-55 (2003).

Lin, Y.-C., et al., "A poly-methylmethacrylate electrophoresis microchip with sample preconcentrator," Journal of Micromechanics and Microengineering, 11, pp. 189-194 (2001).

Medintz, I. L., et al., "Microfabricated capillary array electrophoresis DNA analysis systems," Journal of Chromatograpy A., 924, pp. 265-270 (2001).

Mueller, O., et al., "A microfluidic system for high-speed reproducible DNA sizing and quantitation," Electrophoresis 2000, 21, pp. 128-134 (2000).

Paegel, B. M., et al., "Microfluidic devices for DNA sequencing: sample preparation and electrophoretic analysis," Current Opinion in Biotechnology, 14, pp. 42-50 (2003).

Song, J. M., et al., "Integrated circuit microchip system with multiplex capillary electrophoresis module for DNA analysis," Analytica Chimica Acta, 466, pp. 187-192 (2002).

Ueda, M., et al., "Electrophoresis of long DNA molecules in linear polyacrylamide solutions," Biophysical Chemistry, 71, pp. 113-123 (1998).

Ueda, M., et al., "Imaging of a band for DNA fragment migrating in microchannel on integrated microchip," Materials Science and Engineering C, 12, pp. 33-36 (2000).

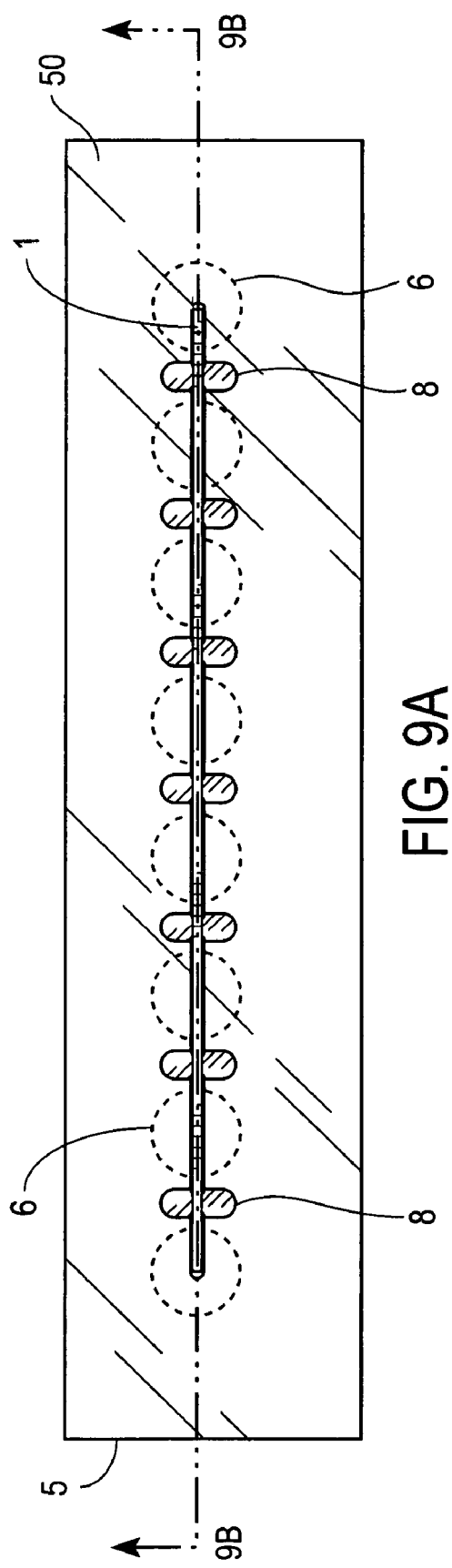
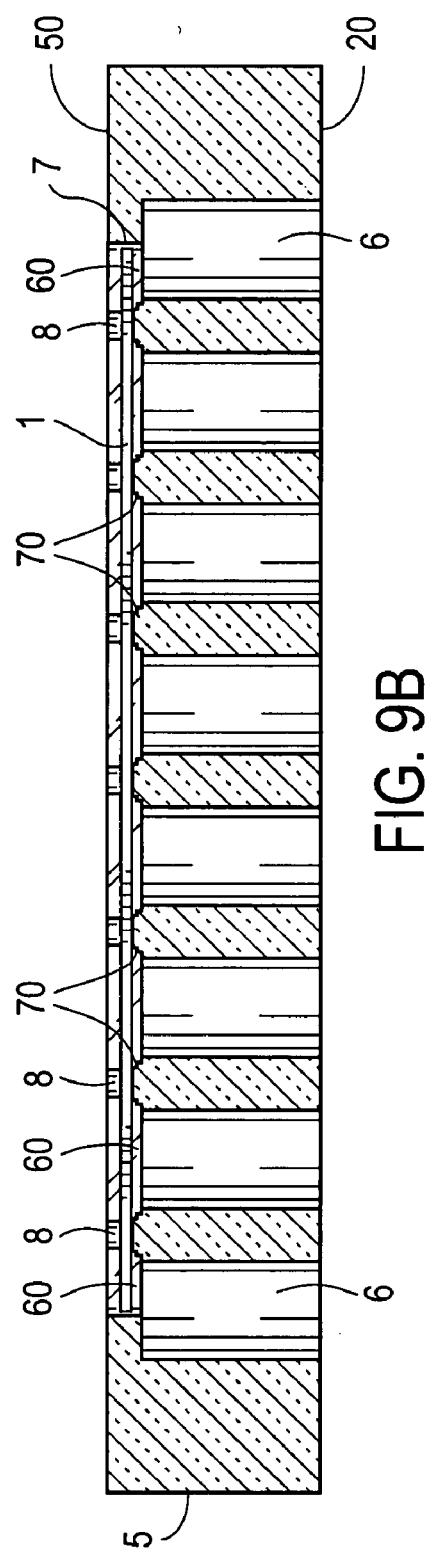
FIG. 9A
FIG. 9B

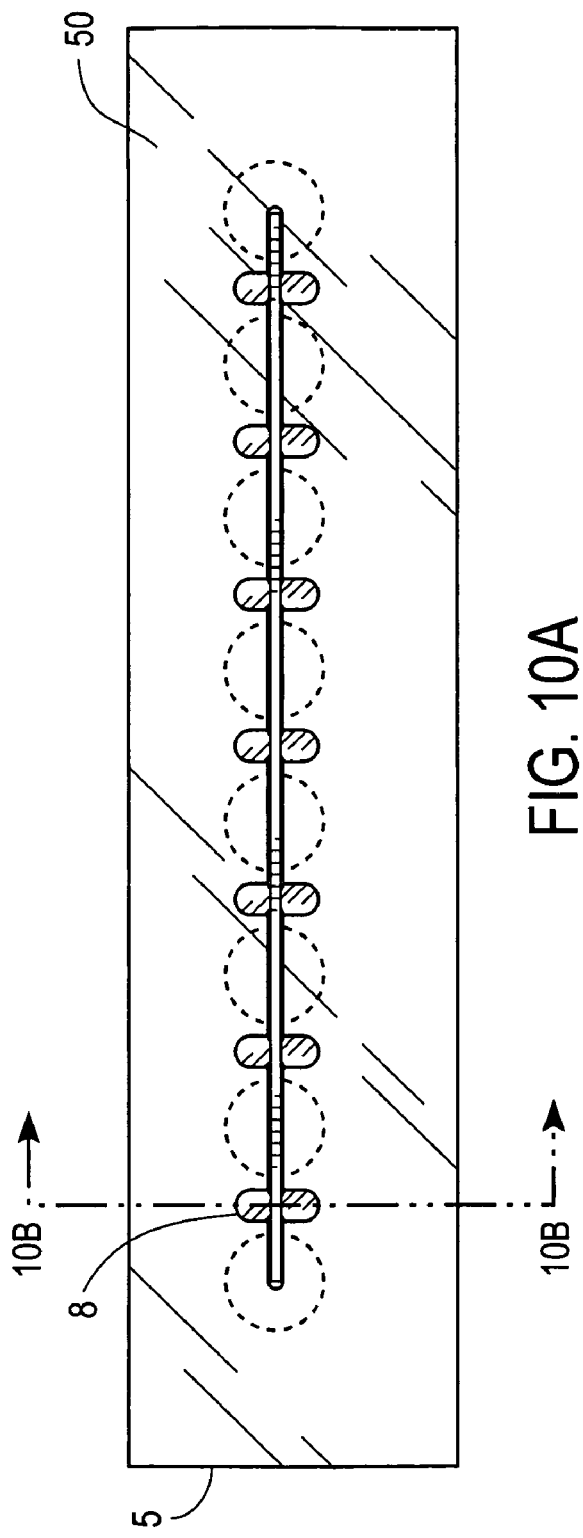
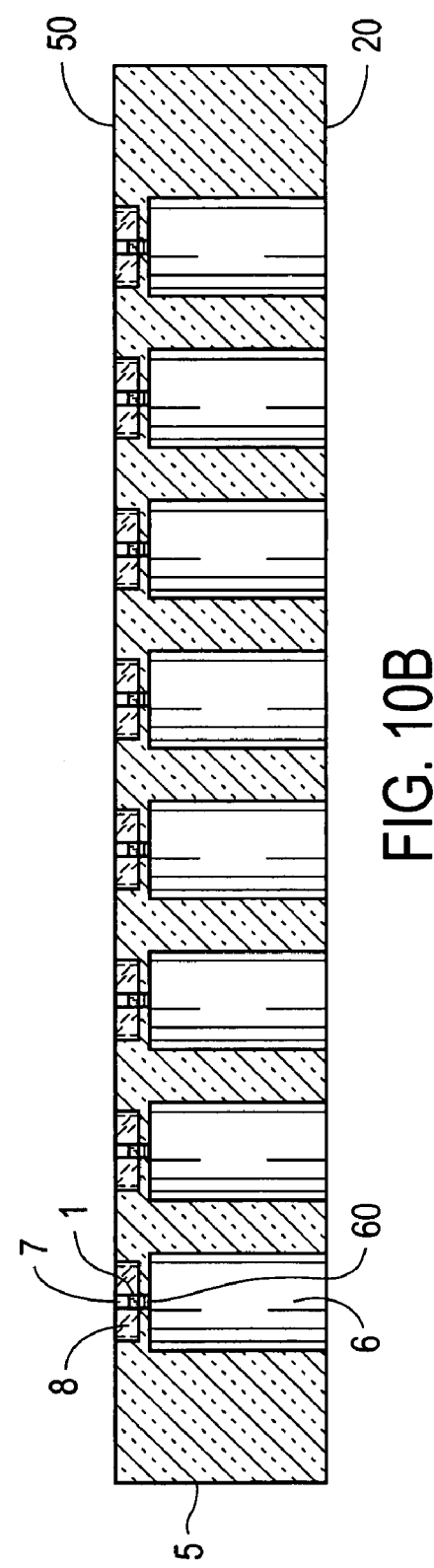
FIG. 10A
FIG. 10B

CAPILLARY ELECTROPHORESIS DEVICES

FIELD OF INVENTION

The present invention relates to a capillary electrophoresis device, more particularly, relates to a capillary electrophoresis device implementing a microfabricated capillary electrophoresis chip being packaged into an injection-molding plastic structure for sample loading and electrophoresis function, as well as a method for preparing the microfabricated capillary electrophoresis chip and the capillary electrophoresis device.

BACKGROUND

Capillary electrophoresis is a technique for moving samples of interest through a solution filled capillary by means of an electric field. In such a way, molecules of different mobilities are separated into distinct zones for detection. In the 1990's, significant research effort in the field of capillary electrophoresis was focused on implementation of such capillary electrophoresis devices in microfabricated formats. Such formats provided significant advantages in terms of precision. As a result, micromachining and miniaturization of such devices was established and many applications of such devices subsequently arose in the literature over the next ten years. Such devices are capable of providing fast, efficient separation results for double stranded DNA chromatography, single stranded DNA chromatography, protein analysis and many other applications.

Central to the efficiency of such devices is channel length. For instance, in applications such as DNA sequencing, a longer reading length is important to the throughput and speed of the entire sequencing effort. Devices with separation channels varying from 1 cm up to 10 cm have been demonstrated within the art. However, these microfabrications still suffer some drawbacks. First, microfabrication with long channel length requires large size devices, resulting in expensive fabrication costs. By contrast, low cost microfabrication is dependent on economy of scale, in which hundreds to thousands of devices per wafer are constructed.

To achieve long channel lengths and still maintain a reasonable device area, one has to produce a separation channel that is folded in a serpentine configuration or curved in a spiral configuration. Unfortunately, such curved channels inevitably reduce the efficiency of the overall separation compared with that of a straight separation channel.

Long channel lengths are not the only factor requiring large chip sizes. The drilling process that drills holes through the substrate layers to access the microchannels also increases the device size. Although drilling in glass substrates can be performed to diameter less than 0.5 mm, typically capillary electrophoresis devices employ holes larger than 1 mm for handling purposes.

Given the above background, what is needed in the art are improved capillary devices and methods for making such devices.

SUMMARY OF THE PRESENT INVENTION

The present invention provides capillary electrophoresis devices featuring long straight channels as well as microfabrication methods for making such device that minimize device size. Another aspect of the present invention is the provision of capillary electrophoresis devices featuring long and straight channels that allow for the addition of liquid access to such channels. Still another aspect of the present invention is the provision of methods for preparing a capillary electrophoresis chip as well as a capillary electrophoresis device that employs long and straight channels, in which the device size is considerably reduced therefore lowering the cost of manufacturing the microfabrication device.

Still another aspect of the present invention is the provision of a capillary electrophoresis chip that is constructed from glass and silicon using microfabrication techniques. Another aspect of the present invention provides a capillary electrophoresis device that uses an injection molding plastic structure to package the capillary electrophoresis chip and to support sample loading, therefore lowering the manufacturing costs.

Accordingly, to achieve the above mentioned aspects of the invention, the present invention provides a capillary electrophoresis device comprising a device body structure having an upper surface and a bottom surface. A plurality of reservoirs is arrayed on the upper surface for loading a sample. A plurality of rows of grooves is transversely defined on the bottom surface. The rows of grooves are connected with the reservoirs. At least a capillary electrophoresis chip is disposed in the device body structure. The capillary electrophoresis chip comprises a glass substrate having a straight main separation channel, an injection channel, and a plurality of sample transport channels defined thereon. The capillary electrophoresis chip further comprises a coating layer for protectively covering the glass substrate. A plurality of access holes are defined on the coating layer. The access holes are adaptive for ensuring liquid communication between the main separation channel, the injection channel, the sample transport channels and the reservoirs. The capillary electrophoresis chip is hermetically embedded into the grooves defined on the bottom surface of the device body structure. The access holes are capable of being oriented towards the reservoirs for liquid communication.

The inventive apparatus further comprises means for applying and actively controlling a first set and a second set of electric potentials at each of the reservoirs. The first set of electric potentials is adapted to drive the sample from the transport channel into the injection. The second set of electric potentials is adapted to drive a portion of the sample down the main separation channel.

The present invention also provides the manufacturing process for preparing the capillary electrophoresis device. In the manufacturing process, predetermined injection-molding plastic structure is prepared. Further, the capillary electrophoresis chip is prepared. The capillary electrophoresis chip is hermetically embedded into the injection-molding plastic structure.

The present invention also provides a manufacturing process for preparing the capillary electrophoresis chip. This process comprises the following steps. A plurality of capillary channels is defined on a glass substrate. The capillary channels are etched to a predetermined depth. The glass substrate is coated with a layer of dielectric film. The dielectric film is collated with a layer of patterned thick film. A plurality of access holes is formed in the dielectric film.

These and other objectives, features, and advantages of the present invention will become apparent from the following detailed description, the accompanying drawings, and the appended claims.

BRIEF DESCRIPTION OF THE DRAWINGS

FIG. 9A illustrates an enlarged view of the perspective of FIG. 8A showing the bottom surface of the device body structure after placement of a capillary chip into a groove in accordance with an embodiment of the present invention.

FIG. 9B illustrates a horizontal side-view perspective of the view illustrated in FIG. 9A in accordance with an embodiment of the present invention.

FIG. 10A illustrates an enlarged view of the perspective of FIG. 8A showing the bottom surface of the device body structure after placement of a capillary chip into a groove in accordance with an embodiment of the present invention.

FIG. 10B illustrates a vertical side-view perspective of the view illustrated in FIG. 10A in accordance with an embodiment of the present invention.

Like reference numerals refer to corresponding parts throughout the several views of the drawings.

DETAILED DESCRIPTION OF THE PREFERRED EMBODIMENTS

Figure 1:
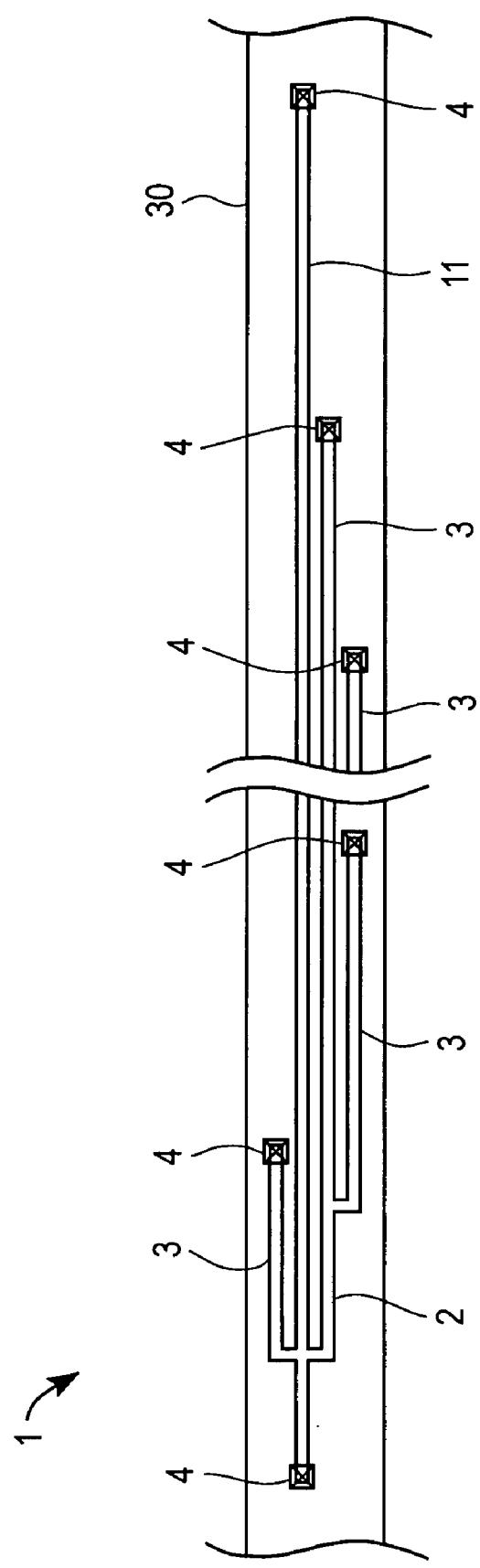
FIG. 1 illustrates a side view of the microfabricated capillary electrophoresis chip in accordance with an embodiment of the present invention.

Referring to FIGS. 1 and 2, the capillary electrophoresis device according to the first preferred embodiment of the present invention is illustrated. The capillary electrophoresis device comprises a device body structure 5 having an upper surface 20 and a bottom surface (not shown in FIG. 2). A plurality of reservoirs 6 is arrayed on upper surface 20. Each reservoir 6 is for loading a liquid sample. A plurality of rows of grooves is transversely defined on the bottom surface to be connected with the reservoirs 6.

At least one capillary electrophoresis chip 1 is disposed in device body structure 5. Capillary electrophoresis chip 1 comprises a substrate 30 (e.g., glass) having a straight main separation channel 11, an injection channel 2, and a plurality of sample transport channels 3 defined thereon. The capillary electrophoresis chip 1 further comprises a coating layer for protectively covering the glass substrate. A plurality of access holes 4 are defined in this coating layer. Access holes 4 are adaptive for ensuring liquid communication between main separation channel 11, injection channel 2, sample transport channels 3 and reservoirs 6 in such a manner by hermetically embedding the capillary electrophoresis chip 1 into the grooves 7 defined on the bottom surface of the device body structure 5 such that access holes 4 are into reservoirs 6. In this configuration, the bottom of reservoirs 6 are in fluid communication with access holes 4.

As shown in FIG. 1, the capillary electrophoresis chip 1 comprises a straight main separation channel 11, an injection channel 2, and a plurality of sample transport channels 3. According to the first preferred embodiment, the channel width is 50 microns with 50 micron spacing, and access holes 4 are at 60 microns wide. At the same time, the percentage of device area used for the channel structure is 24%.

As will be described in detail below, there are plurality dielectric thin films 306 (FIG. 17) deposited on the surface of substrate 30. These dielectric thin films 30 can be silicon dioxide, silicon nitride, etc. Besides providing the dielectric property, the thin films 306 protect channels from environment pollution. It is noted that access holes 4 are opened on the dielectric films to allow samples and buffers to be transported between channels and reservoirs 6, which are in liquid communication with channels, for loading samples through access holes 4. After the capillary channels are filled with suitable buffer, a voltage field is applied and controlled along the sample transport channels 3, an injection channel 2, and separation channel 11. Then the samples are transported through the sample transport channels 3, the injection channel 2, and be separated along the separated channel 11. In some embodiments, capillary electrophoresis chip 1 is about 3.2 cm long and 0.05 cm wide. In preferred embodiments, after capillary electrophoresis chip 1 is packaged into device body structure 5, there are eight total fluidic reservoirs 6 available to the chip.

As will be discussed in further detail below, the present invention further includes means for applying and actively controlling a first and a second electric potential at each of reservoir 6. The first electric potential is adapted to drive a sample in a reservoir 6 from transport channel 3 into injection channel 2. The second electric potential is adapted to drive a portion of the sample down main separation channel 11. In this capacity, dielectric layer 306 helps prevent short circuiting between electrodes placed in different reservoirs 6.

In short, the capillary electrophoresis device comprises a capillary electrophoresis chip 1 and a device body structure 5 for packaging the capillary electrophoresis chip 1 (CE chip 1), and for sample and buffer loading.

Figure 2A:
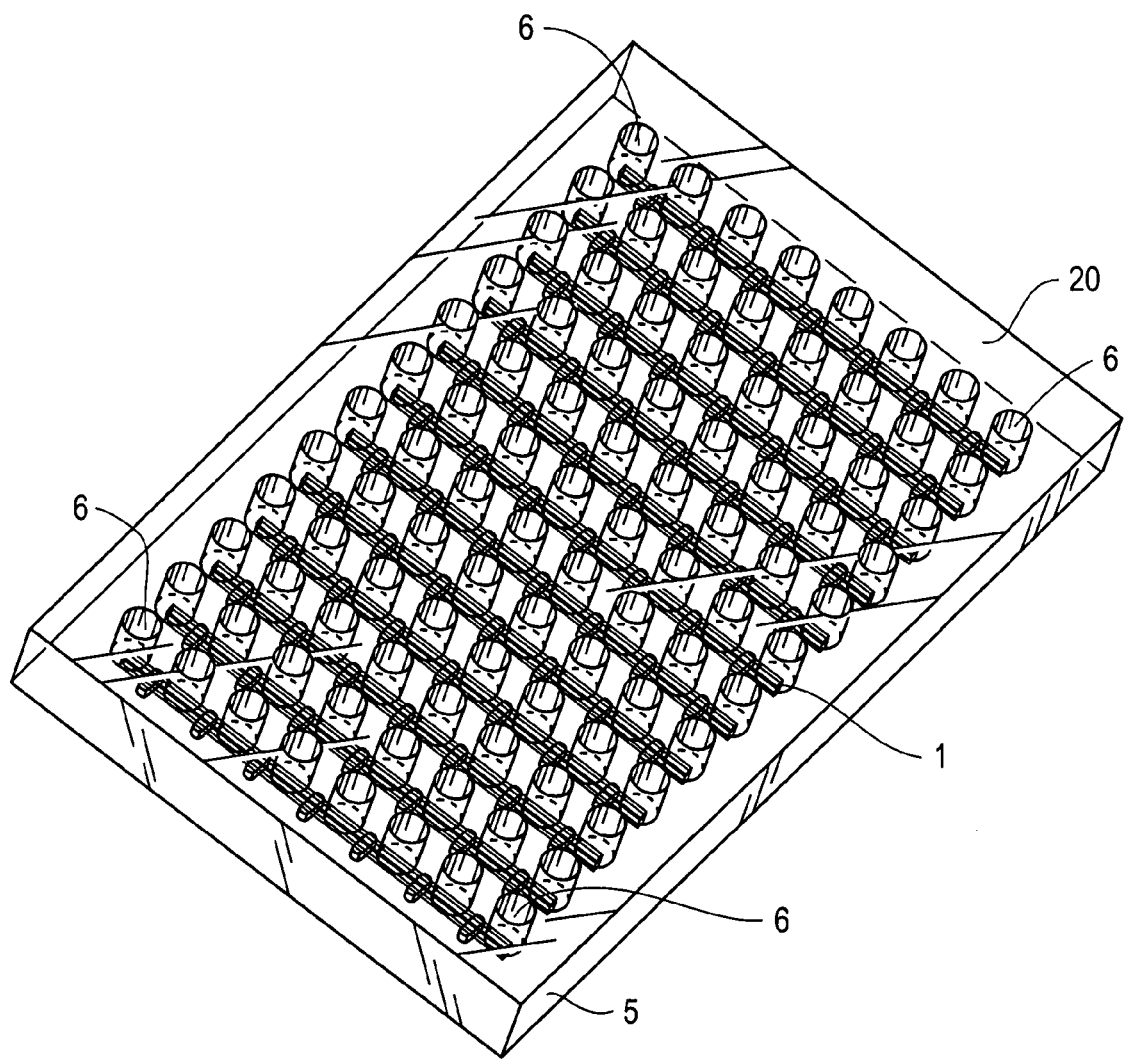
FIG. 2A is a perspective view of an exemplary capillary electrophoresis device illustrating a plastic structure holding a plurality of microfabricated capillary electrophoresis chips in accordance with an embodiment of the present invention.
Figure 2B:
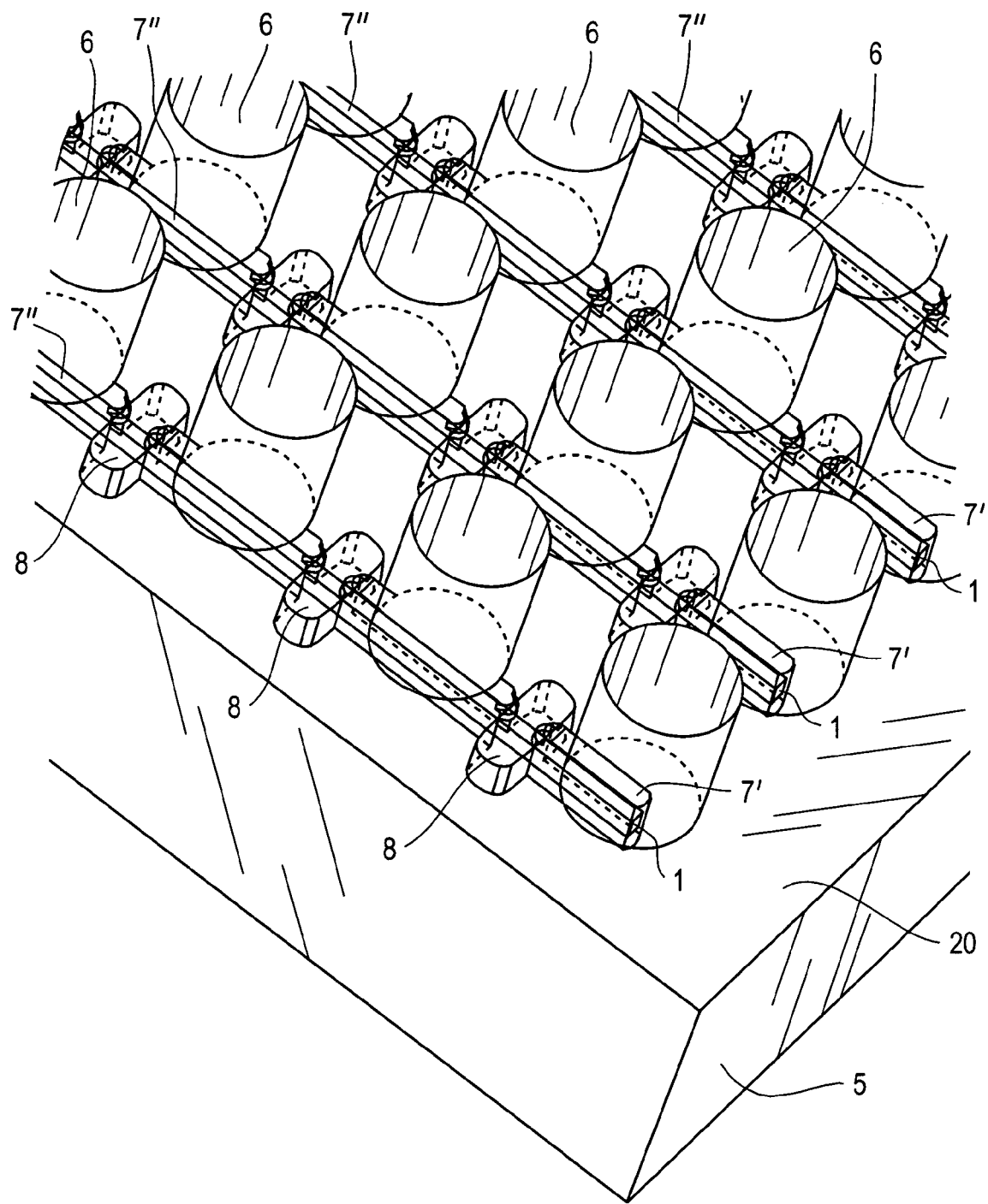
FIG. 2B is an enlarged view of the perspective of FIG. 2A, showing the features of the grooves in the plastic structure for holding the microfabricated capillary electrophoresis chips in accordance with an embodiment of the present invention.

As shown in FIGS. 2A and FIG. 2B, CE chip 1 is packaged in the device body structure 5. According to the preferred embodiment of the present invention, device body structure 5 has an upper surface 20 and a bottom surface. A plurality of reservoirs 6 is arrayed in a matrix manner on upper surface 20 of device body structure 5. A plurality of rows of grooves 7'–7" are transversely defined on the bottom face of device body structure 5 for receiving capillary electrophoresis chip 1. It is noted that a matrix of half-moon shaped cavities 8 (bonding agent receiving wells) are also provided on the bottom face of device body structure 5 for sealing the capillary electrophoresis chips 1 to be packaged into device body structure 5 by epoxy or similar curable sealant. In other words, capillary electrophoresis chip 1 is embedded into grooves 7'–7" first, and then sealed into device body structure 5 by filling the gaps between capillary electrophoresis chip 1 and grooves 7 with epoxy or similar curable sealant.

In some embodiments, the interval between any two reservoirs 6 is 4.5 mm, which is consistent with the interval of the traditional 384 well ELISA and microtiter plates. In some embodiments, this form of standard well spacing is used so that samples and buffers can be loaded into reservoirs 6 automatically by standard liquid handling instruments such as x–y plate based robots.

Device Structure Manufacture

Now that an overview of the device body structure 5 has been presented, a more detailed description of how the device structure is manufactured in accordance with one embodiment of the present invention will be presented. It will be noted that the invention is not limited to the order of steps presented. For example, steps 1, 2, and 3 can be performed in any order. In fact, in preferred embodiments, steps 1–4 can be performed in a single step by injection molding. Thus, the provision of steps 1–4 as discrete steps is merely to emphasis particular details of the inventive apparatus and should not be construed as the preferred method of manufacturing the apparatus.

Figure 3A:
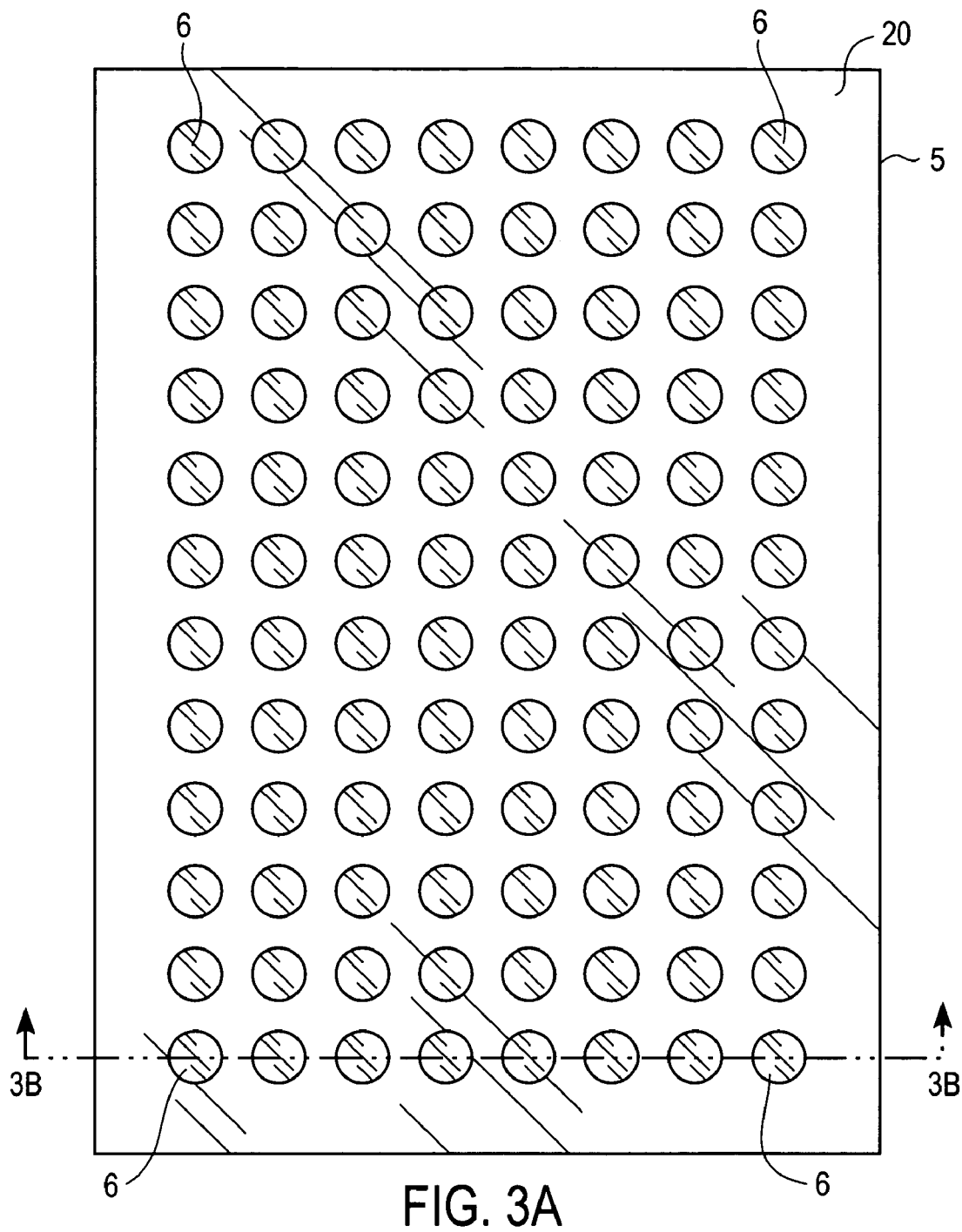
FIG. 3A shows the upper surface of a device body structure in which there is a plurality of wells in accordance with an embodiment of the present invention.
Figure 3B:
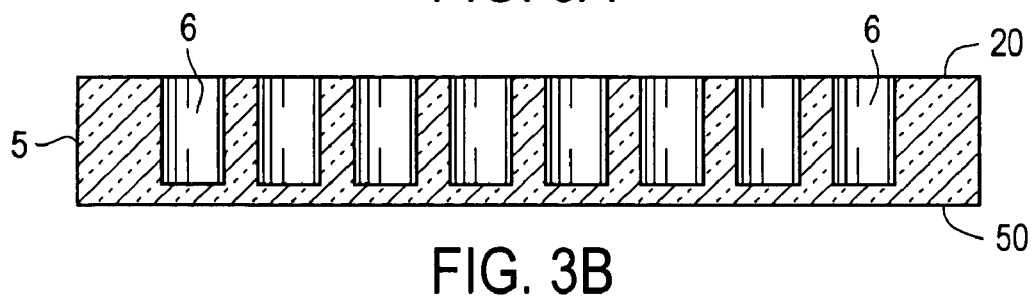
FIG. 3B illustrates a side-view perspective of the view illustrated in FIG. 3A in accordance with an embodiment of the present invention.

Step 1—formation of reservoirs 6. Referring to FIG. 3A, the upper surface 20 of device body structure 5 is shown. A plurality of reservoirs 6 defines 12 rows, where each row has eight reservoirs. In other embodiments, there are more or less rows, with each row including more or less than eight reservoirs. FIG. 3B is a cross sectional view taken across line 3B—3B of FIG. 3A. FIG. 3B shows how each reservoir 6 penetrates into device body structure 5 thereby forming a well. However, as noted in FIG. 3B, reservoirs 6 do not reach all the way to bottom surface 50.

Figure 4A:
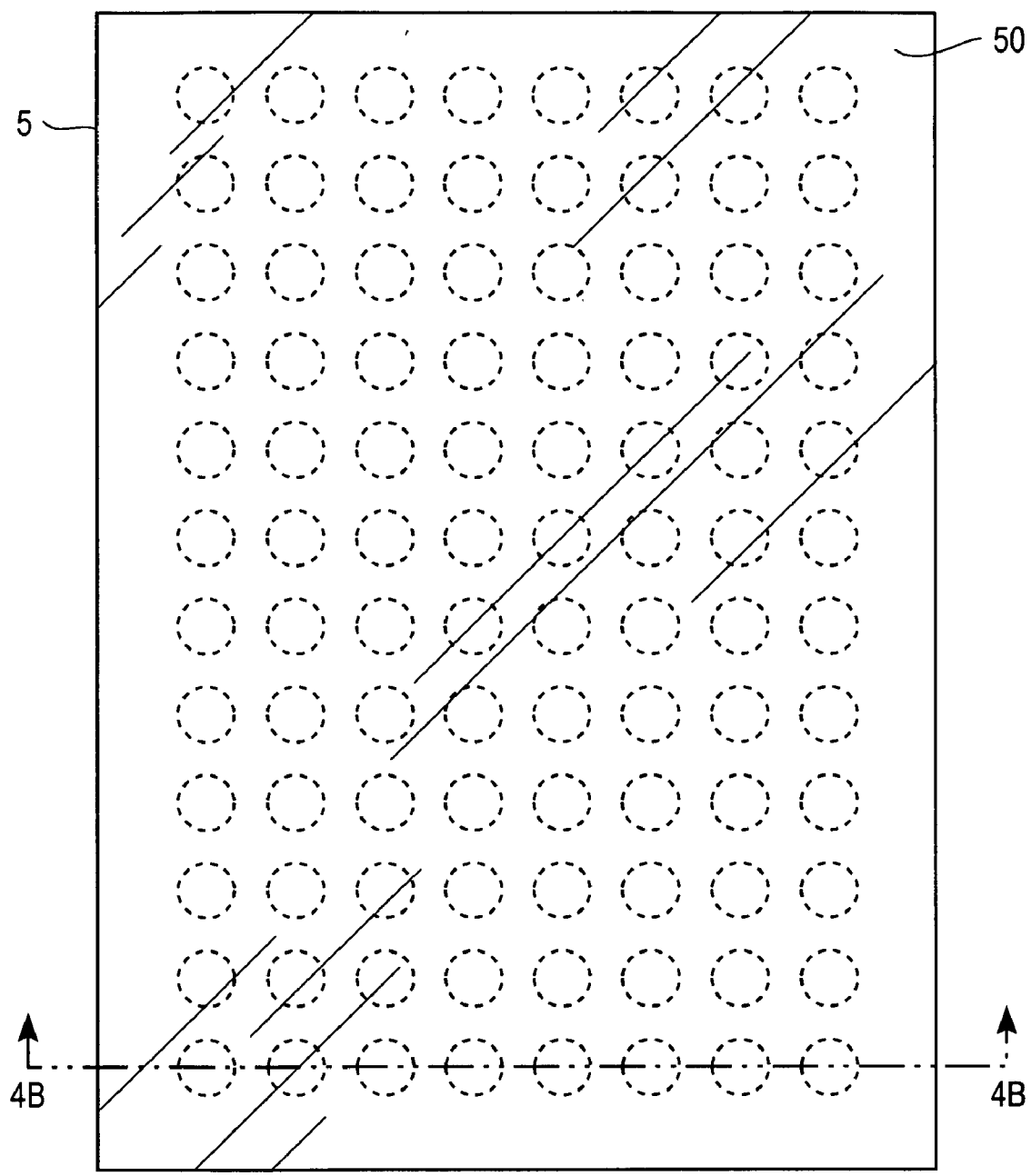
FIG. 4A illustrates the bottom surface of the device body structure before grooves have been scored in the body structure, in accordance with an embodiment of the present invention.
Figure 4B:
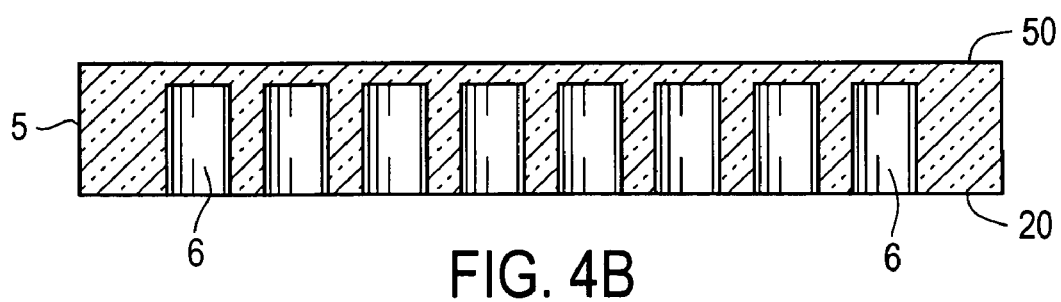
FIG. 4B illustrates a side-view perspective of the view illustrated in FIG. 4A in accordance with an embodiment of the present invention.

Step 2—formation of grooves 7. Referring to FIG. 4A, the bottom surface 50 of device body structure 5 is shown. The location of each reservoir in upper surface 20 is marked by dashed lines. FIG. 4B is a cross sectional view taken across line 4B—4B of FIG. 4A. FIG. 4B shows how each reservoir 6 penetrates into device body structure 5 from upper surface 20 thereby forming a well. However, as noted in FIG. 3B, reservoirs 6 do not reach all the way to bottom surface 50.

Figure 5A:
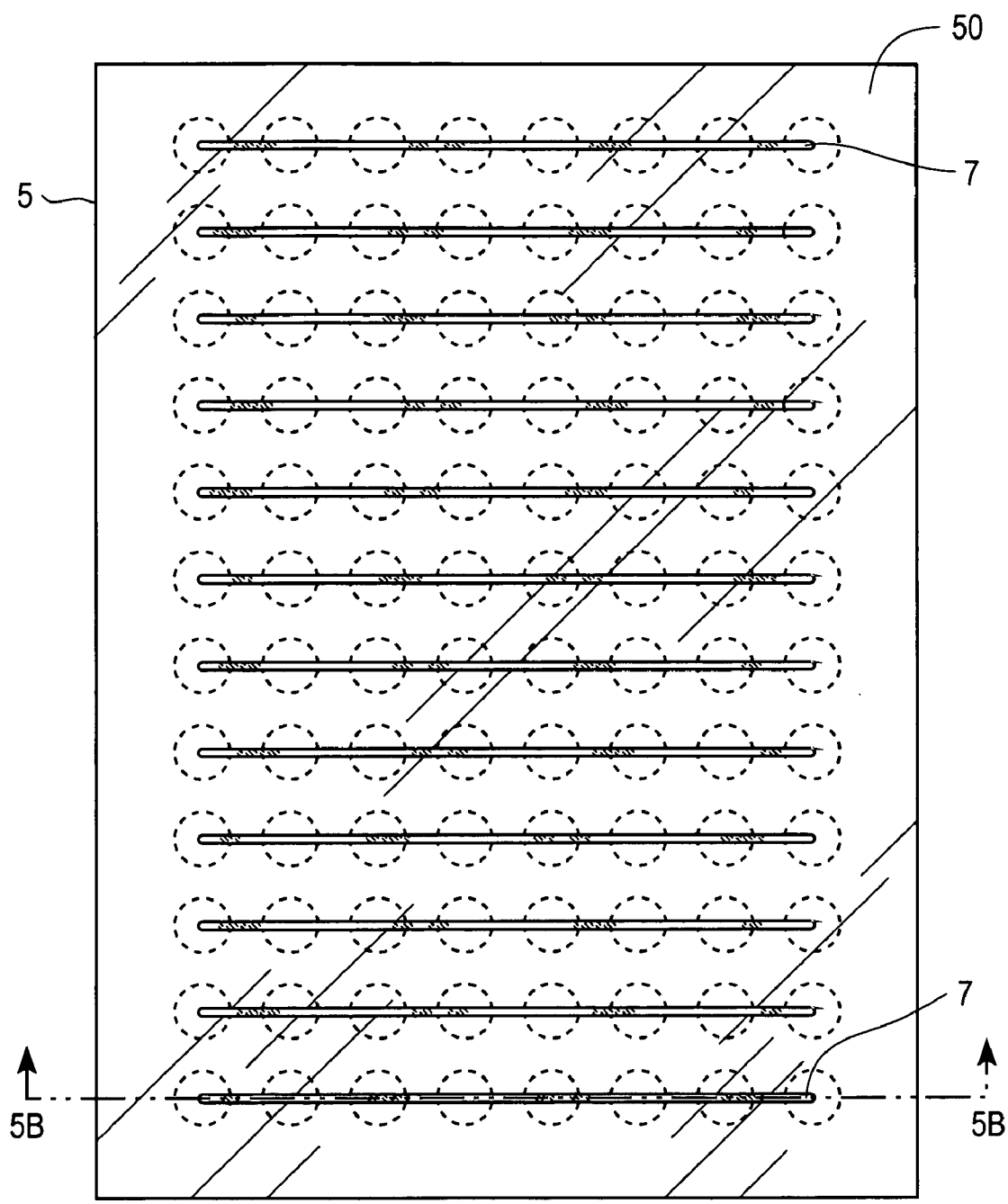
FIG. 5A illustrates the bottom surface of the device body structure after grooves have been scored in the body structure for placement of capillary chips, in accordance with an embodiment of the present invention.
Figure 5B:
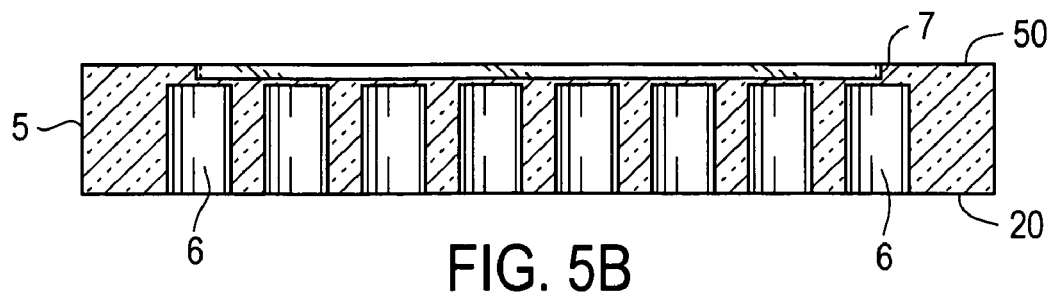
FIG. 5B illustrates a side-view perspective of the view illustrated in FIG. 5A in accordance with an embodiment of the present invention.

Referring to FIG. 5A, a first plurality of grooves 7 are scored into bottom surface 50 of device body structure 5. Ultimately, a CE chip 1 is inserted into each groove 7 as will be described in more detail below. FIG. 5B is a cross-sectional view taken across line 5B—5B of FIG. 5A. FIG. 5B illustrates how each groove 7 is scored into bottom surface 50 but does not quite reach the bottoms of reservoirs 6.

Figure 6A:
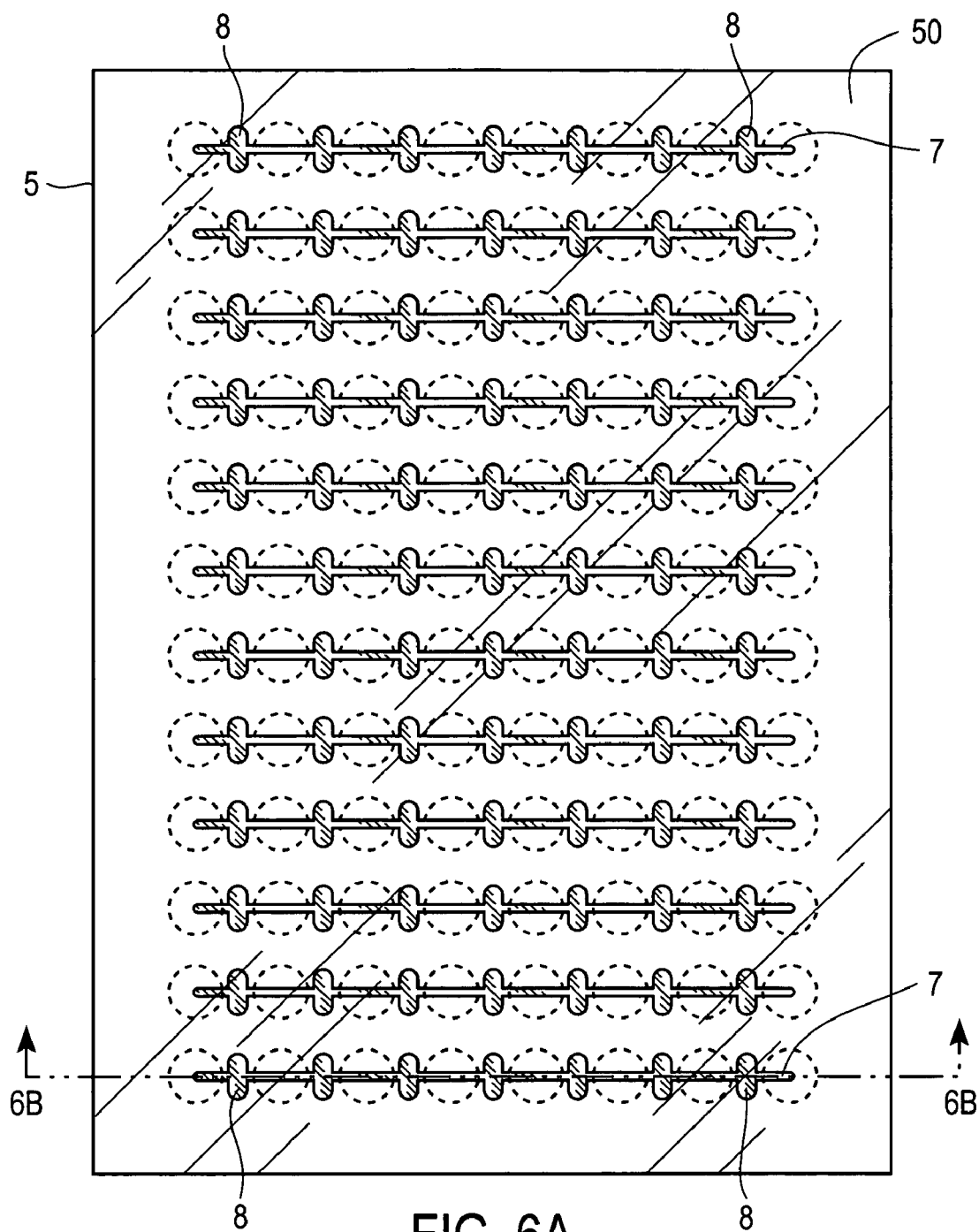
FIG. 6A illustrates the bottom surface of the device body structure after half-moon shaped cavities have been scored in the body structure for placement of bonding agent, in accordance with an embodiment of the present invention.
Figure 6B:
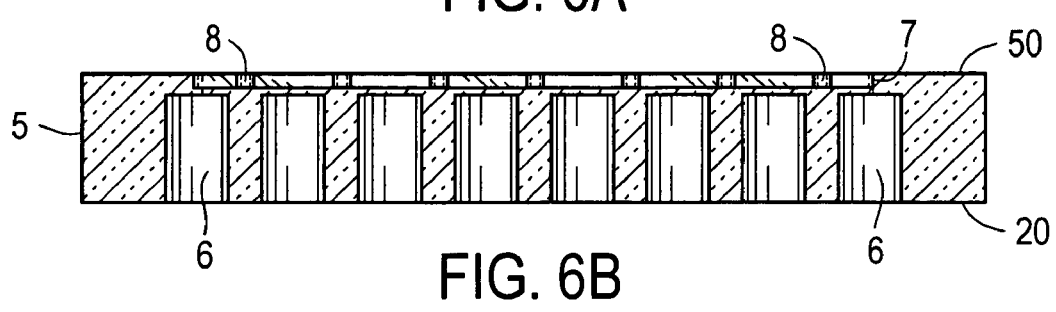
FIG. 6B illustrates a side-view perspective of the view illustrated in FIG. 6A in accordance with an embodiment of the present invention.

Step 3—formation of half-moon shaped cavities 8. In step 3 half-moon shaped cavities 8 (bonding agent receiving wells) are molded into bottom surface 50 of device body structure 5. Details of these half-moon shaped cavities 8 are further illustrated in FIG. 2B. FIG. 6B is a cross-sectional view taken across line 6B—6B of FIG. 6A. FIG. 6B illustrates the positional relationship of each half-moon shaped cavity 8 relative to groove 7 and the bottoms of reservoirs 6. In particular, each half-moon shaped cavity 8 lies between a pair of reservoirs 6.

Figure 7A:
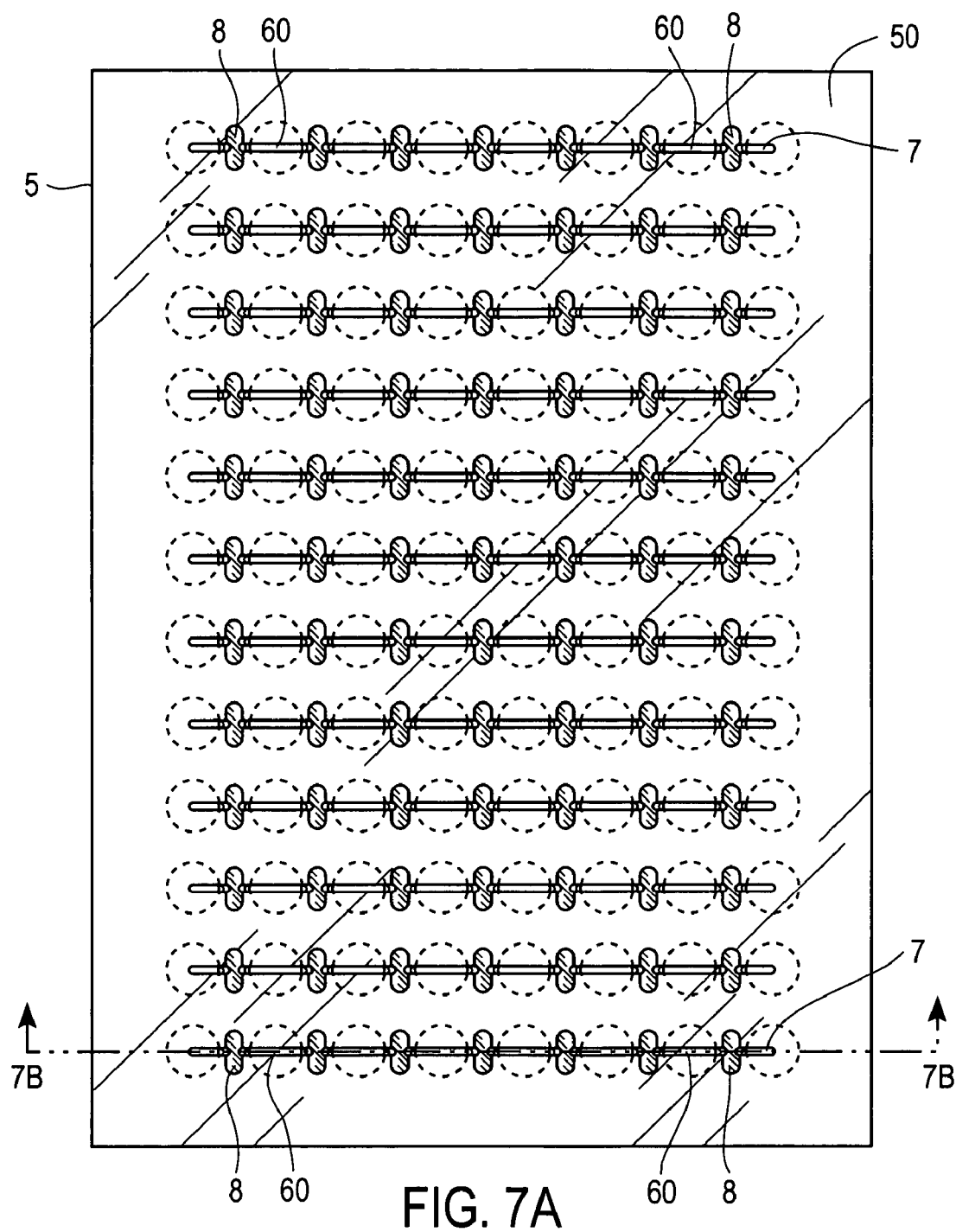
FIG. 7A illustrates the bottom surface of the device body structure after steps between the half-moon shaped cavities and the original grooves of FIG. 5A have been scored in the body structure, in accordance with an embodiment of the present invention.
Figure 7B:
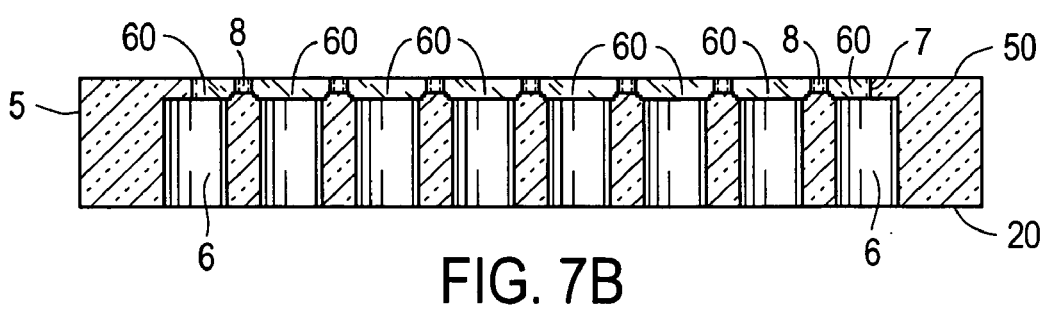
FIG. 7B illustrates a side-view perspective of the view illustrated in FIG. 7A in accordance with an embodiment of the present invention.

Step 4—formation of cuts 60. As illustrated in FIG. 7A, in step 4, cuts 60 are scored into the bottoms of grooves 7 above each reservoir 6. As a result, for each respective reservoir 6, there is a cut 60 that connects a groove 7 to the respective reservoir 6. Each cut 60 has a width that is less than the width of groove 7. FIG. 7B is a cross-sectional view taken across line 7B—7B of FIG. 7A. FIG. 7B illustrates the positional relationship of each cut 60 relative to half-moon shaped cavities 8, groove 7, and the bottoms of reservoirs 6. FIG. 7B illustrates how each cut 60 bores into device body structure 5 thereby connecting groove 7 with the bottom of a corresponding reservoir 6. FIG. 7B illustrates how each cut 60 defines a series of steps from adjacent half-moon shaped cavities 8 to the bottoms of corresponding reservoirs 6. Such steps are illustrated in more detail in FIG. 11A (element 70).

Figure 8A:
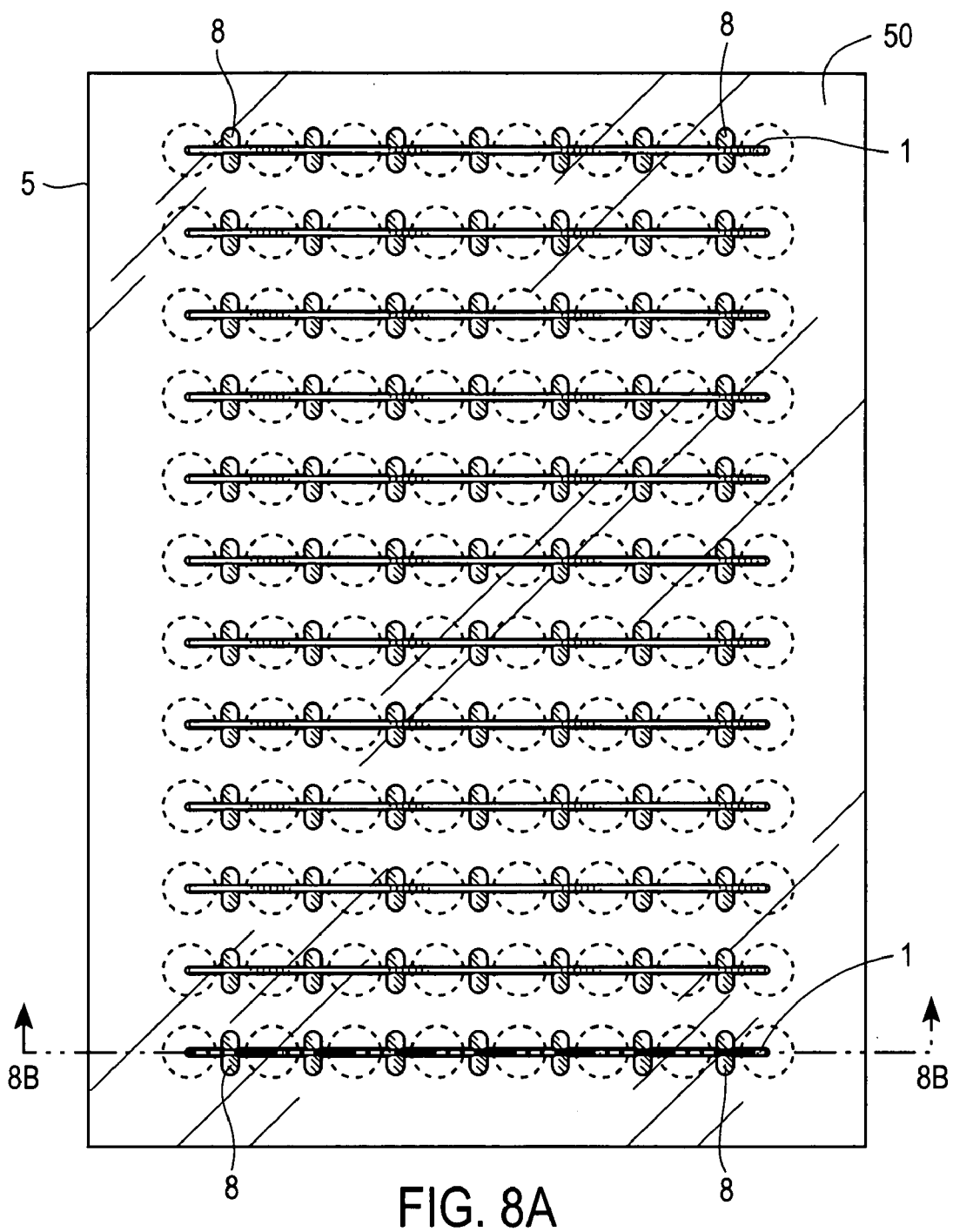
FIG. 8A illustrates the bottom surface of the device body structure after placement of the capillary chips into the grooves in accordance with an embodiment of the present invention.
Figure 8B:
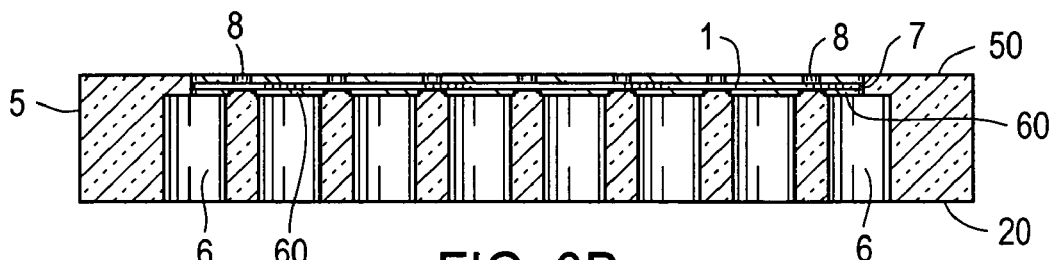
FIG. 8B illustrates a side-view perspective of the view illustrated in FIG. 8A in accordance with an embodiment of the present invention.

Step 5—insertion of CE chip 1 into grooves 7. As illustrated in FIG. 8A, a CE chip 1 is inserted into each groove 7. Therefore, cuts 60 and the features of grooves 7 are no longer visible in the perspective illustrated in FIG. 8A. Each CE chip 1 has a width that is less than the width of groove 7 but is greater than the width of cuts 60. FIG. 8B is a cross-sectional view taken across line 8B—8B of FIG. 8A. FIG. 8B illustrates the positional relationship of CE chip 1 in a groove 7. Further, FIG. 8B illustrates how each cut 60 opens up a face of CE chip 1 to a reservoir 6 that corresponds to the cut 60.

FIG. 9A provides an enlargement of a row from FIG. 8A, with bottom surface 50 facing out of the plane of the figure. In particular, FIG. 9A illustrates how a CE chip 1 fits into a groove 7 and how half-moon shaped cavities 8 are bored into bottom surface 50 in between the profile of adjacent reservoirs 6. Adjacent reservoirs 6 are shown with dashed lines since they open up to upper surface 20, not bottom surface 50. Because CE chip 1 has a width that is almost the same width as groove 7, the features of groove 7 are not evident in FIG. 9A. Moreover, CE chip 1 covers cuts 60 in FIG. 9A so they are also not evident in the figure. However, these details can be seen in FIG. 9B, which is a cross-sectional view taken about line 9B—B of FIG. 9A. FIG. 9B shows how each cut 60 is rimmed by steps 70. Each set of steps 70 leads from a half-moon shaped cavity 8, through cut 60, to the bottom of a reservoir 6 that corresponds to the cut 60.

FIG. 10A provides an enlargement of a row from FIG. 8A, with bottom surface 50 facing out of the plane of the figure. FIG. 10A is identical to FIG. 9A with the exception that there is now a line 10B—10B drawn through a half-moon shaped cavity 8. FIG. 10B is a cross-sectional view taken about line 10B—10B of FIG. 10A. FIG. 10B the positional relationship between a corresponding cut 60 and groove 7, half-moon shaped cavity 8, and CE chip 1. In particular, FIG. 10B illustrates how a cut 60 exposes a surface of CE chip to the bottom of the corresponding reservoir 6.

Figure 11A:
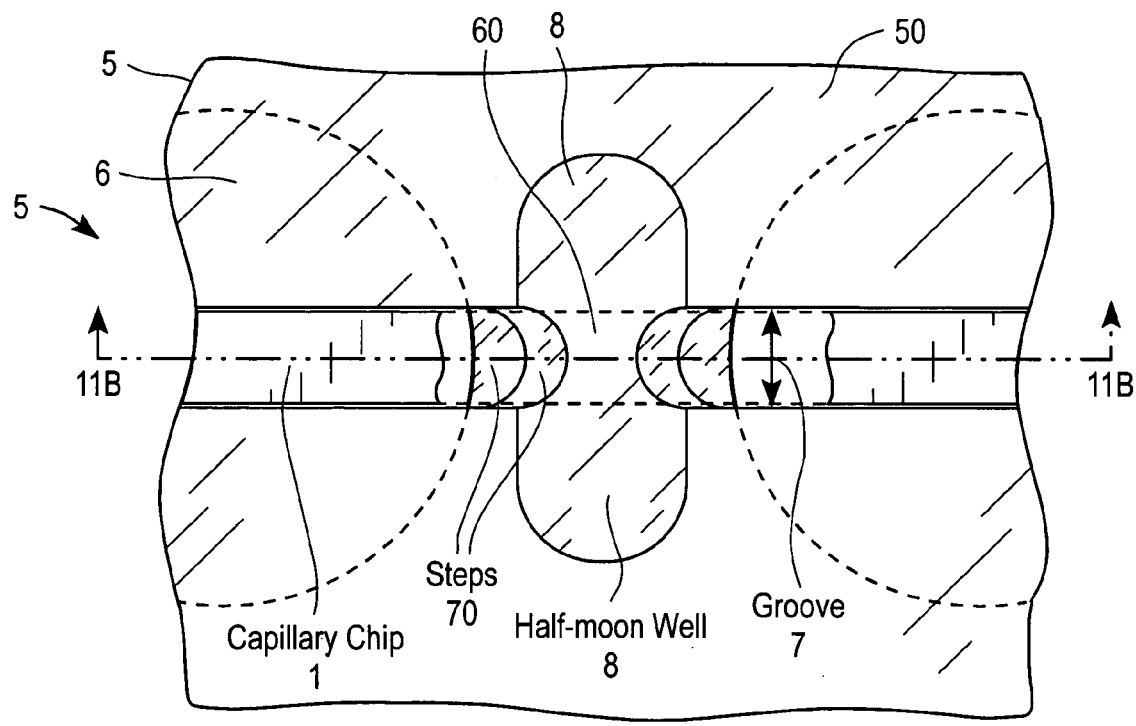
FIG. 11A illustrates an enlarged view of the bottom surface of the device body structure after placement of a capillary chip into a groove, in accordance with an embodiment of the present invention.

FIG. 11A provides an enlargement of the detail of the features found on bottom surface 50. CE chip 1 occupies groove 7. However, in the drawing, portions of capillary chip 1 have been cut away so that the details underneath CE chip 1 can be viewed. In particular, the cut away of CE chip 1 reveals steps 70. Steps 70 define the borders of cuts 60 in groove 7. Cuts 60 lead from the half-moon shaped cavity 8 at the center of the Figure to respective reservoirs 6 on each side of cavity 8.

Figure 11B:
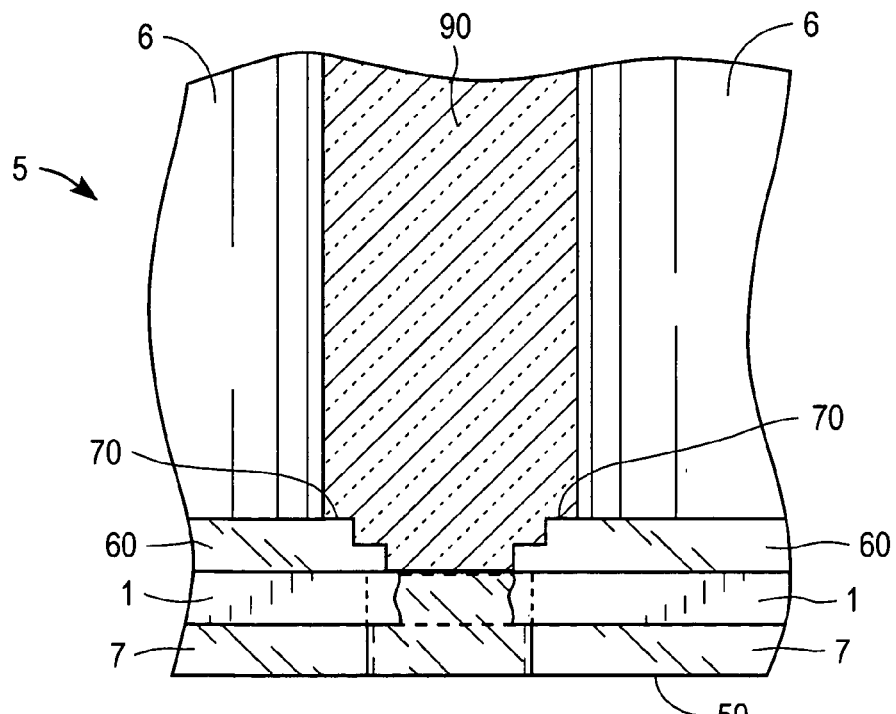
FIG. 11B illustrates a vertical side-view perspective of the view illustrated in FIG. 11A in accordance with an embodiment of the present invention.

FIG. 11B is a cross-sectional view taken about line 11B—11B of FIG. 11A. FIG. 11B illustrates provides additional detail on the positioning of CE chip 1 in a groove 7. FIG. 11B shows CE chip 1 resting at the bottom of groove 7. However, CE chip 1 is cut-away in the same manner shown in FIG. 11A so that additional details of the architecture of the inventive device can be seen. There is a well 6 on the right and left side of the drawing that open up to upper surface 20 of device body structure 5. Groove 7 opens up to bottom surface 50 of device body structure 5. It can be seen that the bottom of groove 7 (which is occupied by CE chip 1) does not extend to the bottoms of reservoirs 6. Accordingly, cuts 60 have been made into groove 7. Each cut 60 corresponds to a bottom of a reservoir 6. Each cut 60 opens a narrow slit of the bottom of a corresponding reservoir 6 thereby exposing CE chip 1 to the reservoir. In preferred embodiments, the width of each cut 60 is less than the width of groove 7. FIG. 11B further shows how steps 70 define the borders of each cut 60. Adjacent cuts 60 and reservoirs 6 collectively define a pillar 90 in device body structure 5. Thus, CE chip 1 rest on a plurality of pillars 90 at the bottom of groove 7. It is these pillars 90 that prevent liquid from one reservoir 6 from seeping into adjacent reservoir 6.

Figure 12A:
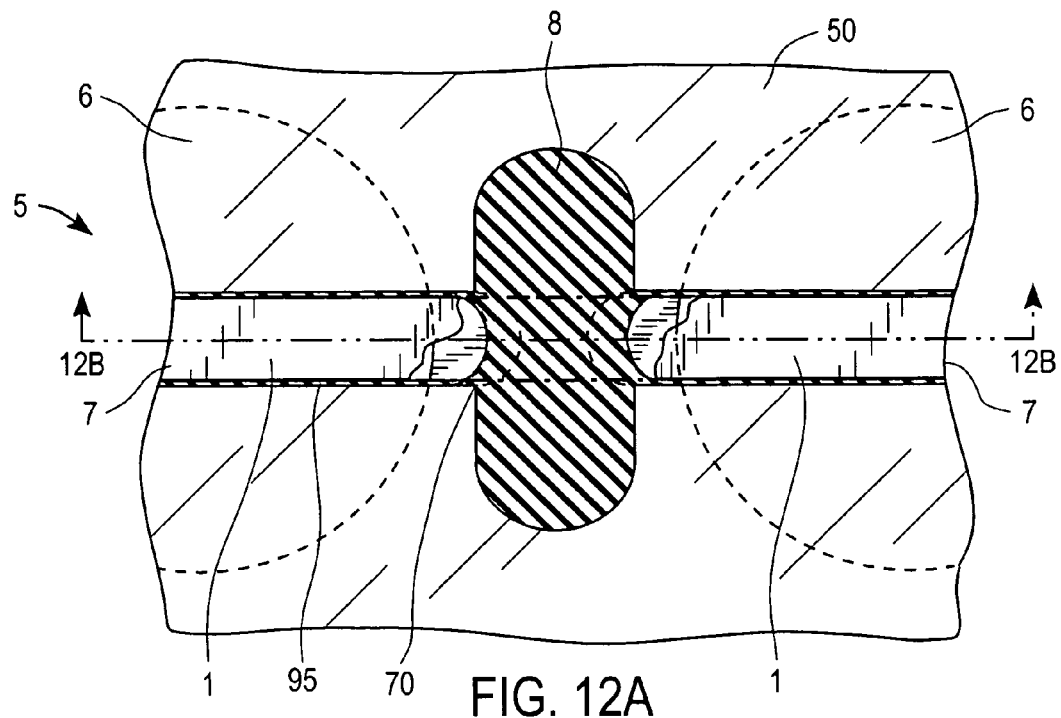
FIG. 12A illustrates an enlarged view of the bottom surface of the device body structure after placement of bonding agent, in accordance with an embodiment of the present invention.

Step 6—Sealing CE chip 1 into device body structure 5. Finally, CE chip 1 is sealed into groove 7 using a bonding agent. FIG. 12A illustrates a blow-up of a portion of bottom surface 50 after the bonding agent has been applied. Bonding agent is added to half-moon wells 8. Because the width of groove 7 is greater than the width of CE chip 1, there is a crack on both sides of CE chip 1. Accordingly, bonding agent seeps from half-moon well 8 into these cracks and then fills the gaps (the cracks) between capillary electrophoresis chip 1 and grooves 7, thereby sealing the capillary electrophoresis chip 1 to be packaged into body structure 5. In FIG. 12A, reservoirs 6 are shown in dashed lines because the reservoirs open to upper surface 20 and not bottom surface 50. CE chip 1 resting in groove 7 can be seen in FIG. 12A. Furthermore, the crack 95 between CE chip 1 and groove 7 can be seen in the cut-away. Crack 95 is filled with bonding agent that seeped into the crack from half-moon well 8. In some embodiments, CE chip 1 has a width of about 500 μm and groove 7 has a width of about 500 μm. In such embodiments, the crack on each side of CE chip 1 will have a width of about 50 μm.

Figure 12B:
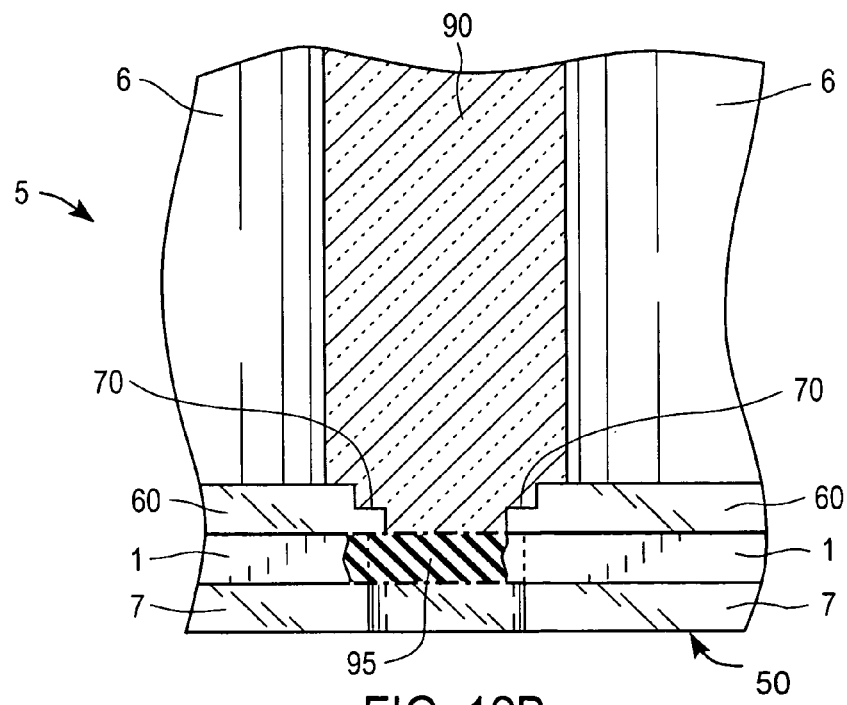
FIG. 12B illustrates a vertical side-view perspective of the view illustrated in FIG. 12A in accordance with an embodiment of the present invention.

FIG. 12B is a cross-sectional view taken about line 12B—12B of FIG. 12A. FIG. 12B illustrates how CE chip 1 rests at the bottom of groove 7. A portion of CE chip 1 has been cut-away revealing a crack 95 between CE chip 1 and a side-wall of groove 7. Crack 95 is filled with bonding agent. Also shown in FIG. 12B is a pair of cuts 60 that respectively adjoin left reservoir 6 and right reservoir 6 to groove 7. Although there is a line demarking the boundary between each cut 60 and the corresponding reservoir 6, in fact such cuts 60 and reservoirs 6 are in fluid communication with each other, thereby exposing the portion of CE chip 1 that includes access holes 4 to reservoirs 6. In fact, in preferred embodiments, there is one access hole 4 exposed by each cut 60. In other words, there is a one-to-one correspondence between access holes 4 and reservoirs 6. In such preferred embodiments, each reservoir 6 is in fluid communication with exactly one access hole 4 in a CE chip 1. FIG. 12B further illustrates how the longitudinal boundaries of cuts 60 are defined by steps 70. Each set of steps 70 leads from half-moon well 8 (shown in FIG. 12A but not FIG. 12B) to the respective bottoms of reservoirs 6. FIG. 12B further illustrates how adjacent cuts 60 and reservoirs 6 collectively define a pillar 90 in device body structure 5. CE chip 1 rest on pillar 90 at the bottom of groove 7.

Additional Embodiments and Features

Figure 14:
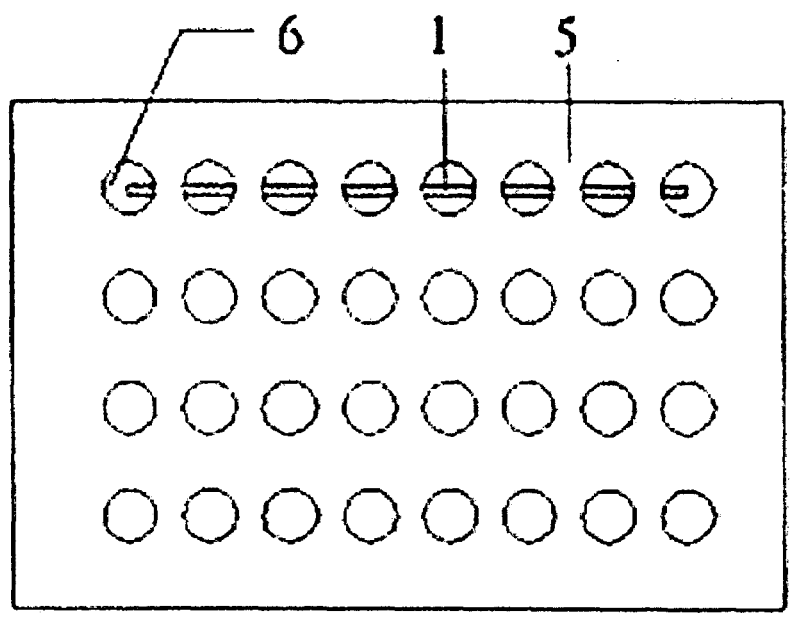
FIG. 14 illustrates a top view of the capillary electrophoresis device according to an embodiment of the present invention.
Figure 15:
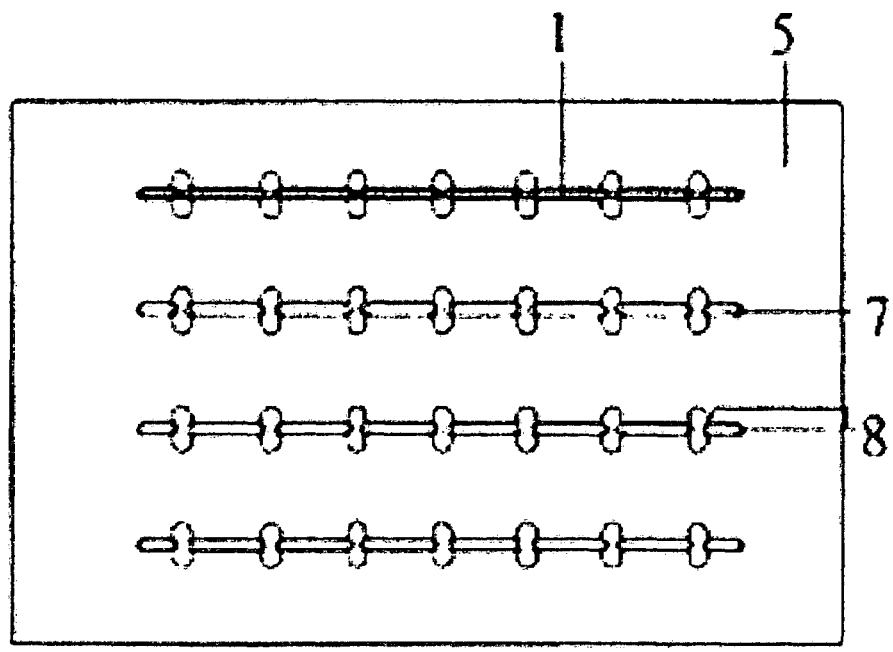
FIG. 15 illustrates a bottom view of a capillary electrophoresis device according to an embodiment of the present invention.
Figure 16:
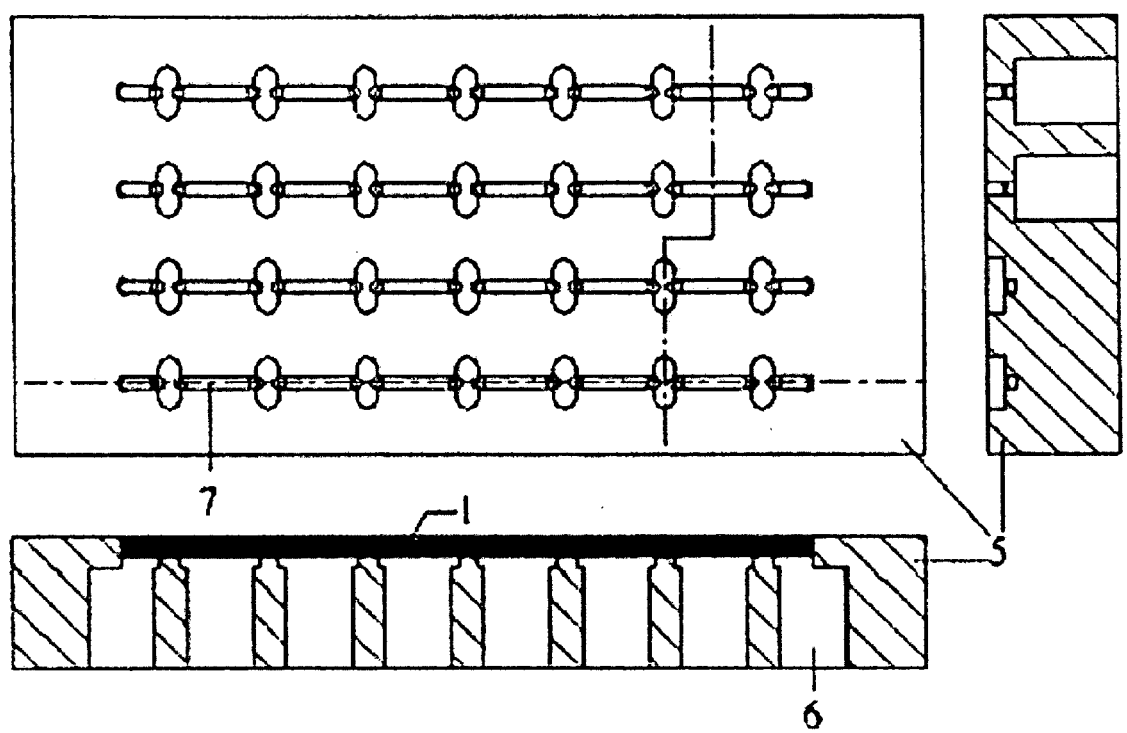
FIG. 16 illustrates a bottom view of a capillary electrophoresis device according to an embodiment of the present invention together with a side section view and a rear section view.

With reference to FIGS. 14–15, according to one embodiment of the present invention, on bottom surface 50 of device body structure 5, there are four rows of grooves 7 and a plurality of half-moon wells 8 disposed in a geometrically designed manner. Each CE chip 1 can be packaged into one groove 7 by sealing the gaps between CE chip 1 and the wall of groove 7 and the gap between CE chip 1 and the top of groove 7 with epoxy (or similar curable sealant) using capillary forces. According to the top view FIG. 14, there are eight reservoirs 6 used for samples and buffer loading. Each reservoir 6 corresponds to an access hole 4 of CE chip 1. The samples and buffers can flow down to the capillary channels through the bottom of the reservoirs 6 and the access hole 4. Preferably, four reservoirs are filled with the electrophoresis buffer solution to control transportation, injection and separation of samples in the separation channel 11. The remaining four reservoirs are used for individual samples.

Electrode Assembly

Figure 13:
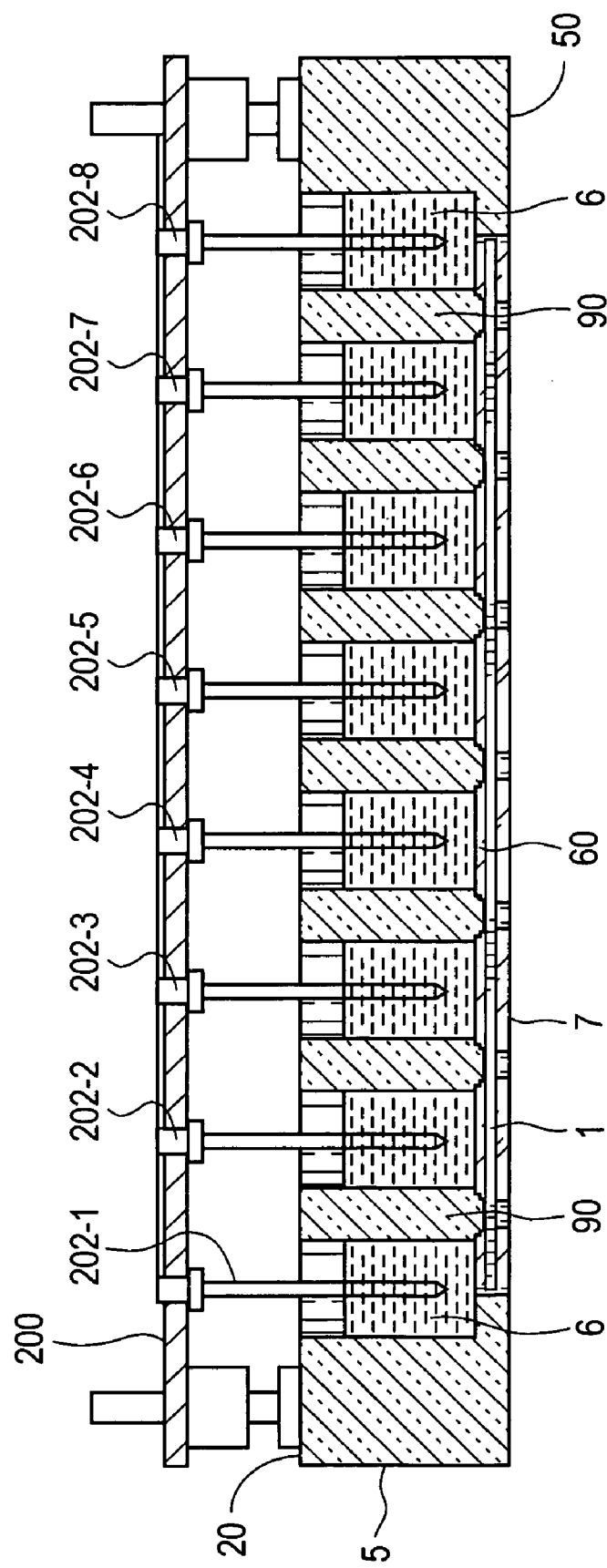
FIG. 13 illustrates a side-view perspective of the inventive apparatus showing an electrode assembly that is used to load one or more samples into an electrophoresis chip and to control the one or more samples once they have been loaded into the chip in accordance with an embodiment of the present invention.

According to preferred embodiments of the present invention, the capillary electrophoresis device further comprises means for applying and actively controlling an electric potential at each of the reservoirs 6 simultaneously. As illustrated in FIG. 13, an electrode plate 200 is introduced while a plurality of electrodes 202 is placed into reservoirs 6 thereby making contact with fluid in such reservoirs. A first set of potentials are applied to the reservoir electrodes 202 to electrophoretically drive a sample in a reservoir from a transport channel 3 into injection channel 2. Next, a second set of potentials are applied to drive a small fraction of the sample down separation channel 11.

FIG. 13 illustrates the combination of electrode plate 200, device body structure 5 and CE chip 1. Although not seen in FIG. 13, electrode plate 200 extends in a third dimension in preferred embodiments and includes individual electrodes 202 for each reservoir in device body structure 5. The voltage field can be applied through these electrodes to the capillary channels.

Process for Preparing and Applying a Capillary Electrophoresis Device

The present invention further provides a process for preparing and applying said capillary electrophoresis device, wherein the process comprises the following steps (i) preparing a predetermined injection-molding plastic structure 5, (ii) preparing a capillary electrophoresis chip 1, (iii) hermetically embedding the capillary electrophoresis chip 1 into the injection-molding plastic structure 5, (iv) loading a sample and a buffer into reservoirs 6 of the plastic structure 5, (v) and providing means to apply and actively control a first set and a second set of electric potentials against the sample for separation and detection along the capillary electrophoresis chip 1.

Figure 17A:
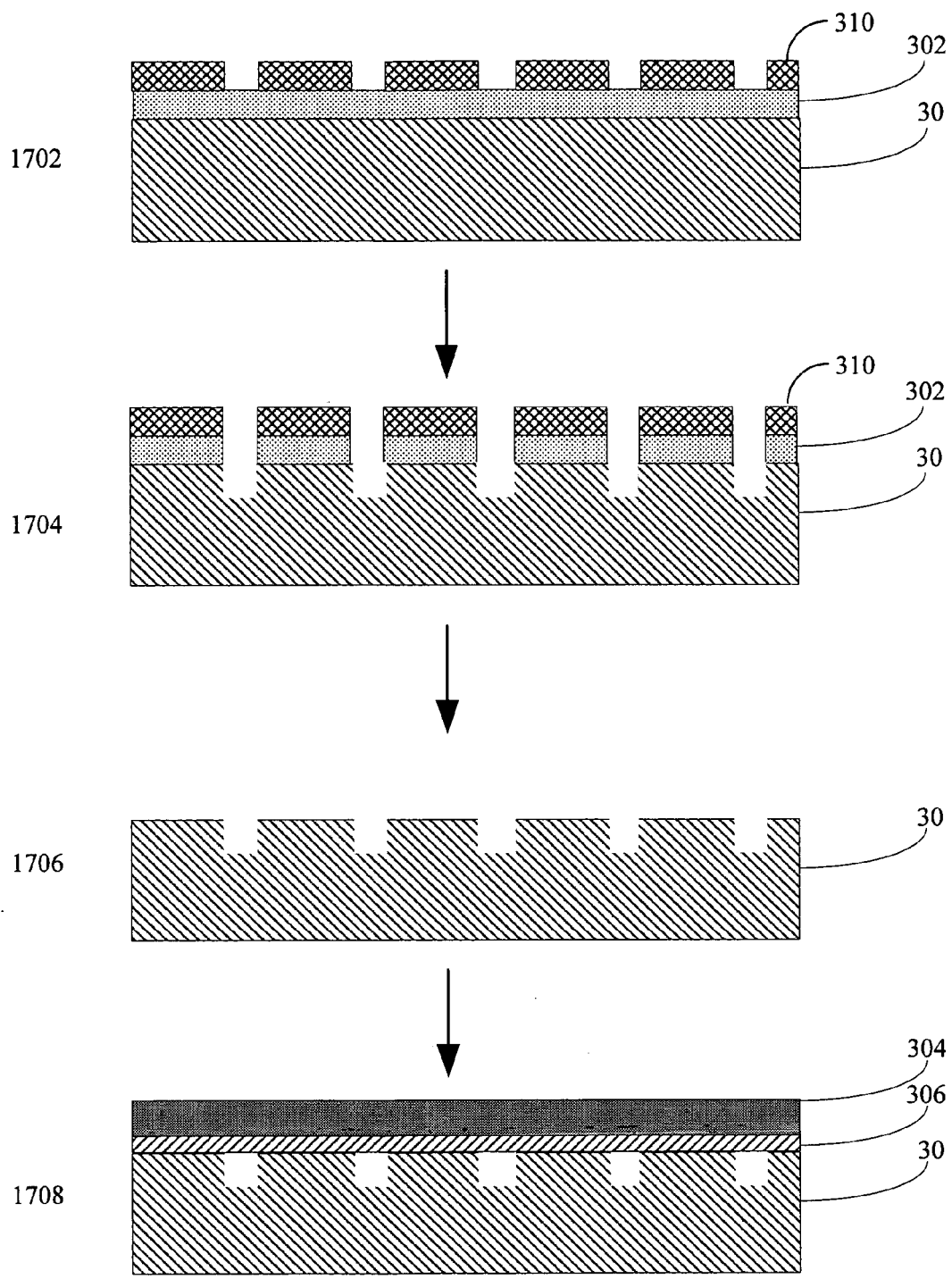
FIGS. 17A–17B illustrate a method of manufacturing a capillary electrophoresis chip in accordance with an embodiment of the present invention.
Figure 17B:
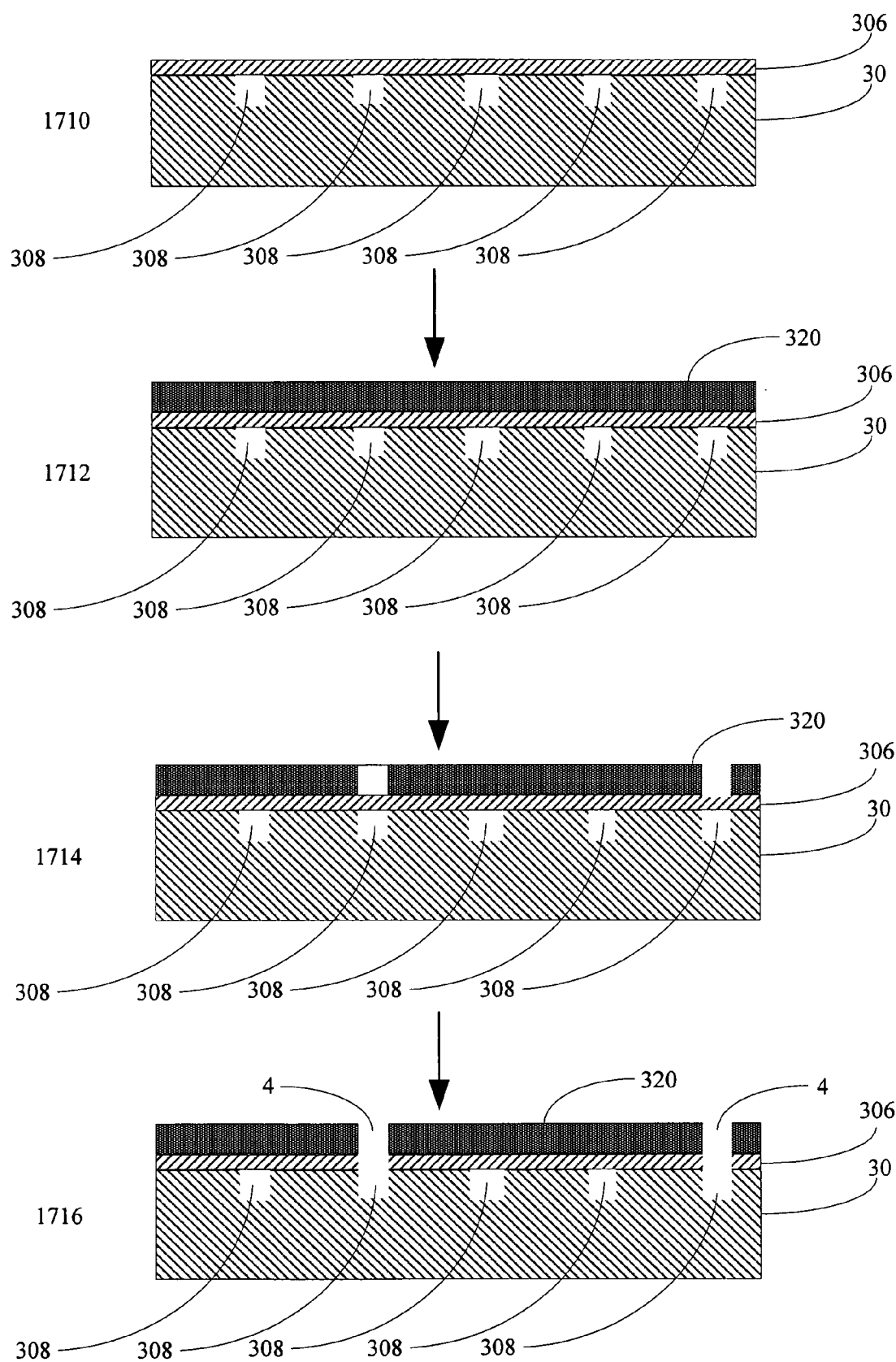

FIG. 17 illustrates the manufacturing process for preparing the microfabricated capillary electrophoresis chip 1 according to the step (ii) of the above-identified process.

Step 1702. In step 1702, a plurality of capillary channels, such as the capillary channels 2, 3, and 11 of FIG. 1, is defined on a substrate 30 using a photoresist 310 to define the pattern in a mask 302. In some embodiments, substrate 36 is made out of glass (e.g. glass, borosilicate glass, aluminosilicate glass, vycor, fused silica, vitreous silica, glass ceramics). In some embodiments, photoresist 310 is a positive photoresist or a negative photoresist. Examples of suitable compounds for photoresist 310 include, but are not limited to, Novolak, poly isoprene, poly-(methylmethacrylate) (PMMA), poly-(methyl isopropenyl ketone (PMIPK), poly-(buten-1-sulfone) (PBS), poly-(trifluoroethylchloroacrylate) (TFECA), copoylymer-(α-cyano ethyl acrylate-α-amido ethyl acrylate (COP PCA), or poly-(2-methyl pentene-1-sulfone) (PMPS). In some embodiments, mask 302 is Cr/Au or polysilicon carbide.

Mask 302 is applied to a clean and dry substrate 30 by a process such as spin coating. Likewise, photoresist 310 can be overlaid onto mask 302 by a process such as spin coating. In some embodiments, photoresist 310 is partially evaporated using a softbake step. A filter that includes the pattern of capillary channels is then aligned against the substrate and photoresist 310 is exposed using the filter. Any type of aligner, including optical and nonoptical aligners can be used. For example contact aligners, proximity aligners, projection aligners, stepper aligners, x-ray aligners—and E-beam aligners can be used. Photoresist 310 is then developed thereby leaving the capillary pattern embedded in photoresist 310 that remains on mask 302 after development. In some embodiments, the photoresist is developed using a basic aqueous solution such as a tetramethylammonium hydroxide (TMAH) solution, NaOH, or KOH.

Step 1704. In step 1704, capillary channels 308 are etched in substrate 30. In some embodiments etching 1704 is performed by chemical wet etching until channels that are about 8 μm to about 20 μm deep have been etched. Any etchant that will etch substrate 30 at a faster rate than mask 302 can be used in step 1704. In preferred embodiments, hydrofluoric acid, HF/HCl, NH$_4$F, buffered oxide etchant (BOE), or similar wet etchant is used.

Step 1706. In step 1706, photoresist 308 is dissolved away. Further, mask 302 is etched off using standard resist stripping techniques. For example, solutions of sulfuric acid and an oxidant (e.g., hydrogen peroxide or ammonium persulfate) can be used. See, for example, Van Zant, *Microchip Fabrication,* 2000, McGraw-Hill, New York, which is hereby incorporated by reference in its entirety.

Step 1708. In step 1708, a silicon wafer 304 coated with a dielectric thin film 306 is bonded to substrate 30. Dielectric thin film 306 can be, for example, silicon nitride or silicon dioxide. Dielectric thin film 306 can be deposited on silicon wafer 304 by chemical vapor deposition (CVD), low pressure chemical vapor deposition (LPCVD), plasma-enhanced chemical vapor deposition (PECVD) or any or another of other deposition techniques known in the art. See, for example, Van Zant, *Microchip Fabrication,* 2000, McGraw-Hill, New York.

Step 1710. After dielectric thin film 306 and silicon wafer coat 304 have been bonded to substrate 30, silicon wafer 304 is dissolved by dry and/or wet etching. using KOH solution, TMAH solution, HF/HNO$_3$, XeF$_2$, EDP, SF$_6$, or similar etchant. In this manner, dielectric thin film 306 is transferred to substrate 30 in such a manner that the thin film covers etched capillary channels 308 (where 308 is any of channels 3, 11, or 2).

Step 1712. In step 1712, a thick film 320 is coated onto dielectric film 306. Useful materials for thick film 320 are polymer based materials, photoresists, polyimides, teflons, etc.

Step 1714. In step 1714 thick film 320 is patterned to form access holes 4 using standard fabrication techniques. See, for example, Van Zant, *Microchip Fabrication,* 2000, McGraw-Hill, New York; Levinson, *Principles of Lithography,* 2001, SPIE Press, Bellingham, Wash.; *Microlithrography, Micromaching and Microfabrication,* Rai-Choudhury ed., 1997, SPIE Press, Bellingham, Wash.; and Madou, *Fundamentals of Microfabrication,* Second Edition, 2002, CRC Press, New York, each of which is incorporated by reference in it entirety. Access holes 4 are vias to the capillaries 308.

Step 1716. In step 1716, a dry etching machine is used to etch dielectric film 306 in the specific holes defined by the pattern in thick film 320 in order to open up access holes in CE chip 1 (See FIG. 1).

Finally, the capillary electrophoresis chip 1 is prepared by the above mentioned process. According to a preferred embodiment, the capillary channels are formed by photolithography and wet etching on a glass substrate. The depth of the capillary channels is about 10 µm. In one embodiment, CE chip 1 length is 3.2 cm and CE chip 1 width is 0.05 cm, and the ratio of the length to the width of the device is 64.

In one embodiment, the step (iv) from above further comprises a step for loading a predetermined reservoir 6 with a buffer. In such instances, four reservoirs 6 are used for controlling the injection and separation of samples in the separation channel 11. In some embodiments, these four reservoirs are filled with the electrophoresis buffer solution. Preferably, a suitable linear polymer solution is used as an electrophoresis buffer solution. Such suitable polymers include linear polyacrylimide, hydroxyethylcellulose, hydroxypropylethylcellulose and the like. The remaining four reservoirs are used for individual samples. Channels 4 in CE chip 1 allow for individual sample transport to the injection channel 2 and separation channel 11. A sample of a mixture of DNA molecules of different sizes (a restriction digest product for example) is then placed in one of the four sample reservoirs.

In step (v) from above, electrodes 202 (FIG. 13) are then placed into the reservoirs 6 in order to make contact with fluid in such reservoirs 6. A first set of potentials are applied to the reservoir electrodes 6 to drive the sample from the transport channel 3 into the injection channel 2 by electrophoresis. This involves applying a voltage potential between a first set of electrodes 202 and a second set of electrode 202, where a set of electrodes is one or more predetermined electrodes 202. In this capacity, dielectric layer 306 prevents short-circuiting between the two sets of electrodes. Next, a second set of potentials are applied to drive a small fraction of the sample down the separation channel 11. This second set of potentials is created by applying a voltage potential between a third sets of electrode 202 and a fourth set of electrode 202. As the molecules separate, they pass over a detection area at the end of separation channel 11 and are detected by fluorescence techniques. After separation is complete, another set of potentials can be applied to perform the analysis on a second sample. This addition set of potentials is applied between a fifth set of electrodes 202 and a sixth set of electrode 202. The application of electric potentials between sets of electrodes 202 in order to load a sample into CE chip 1 and to facilitate separation of the sample is illustrated in Example 1, below with reference to FIGS. 18–21.

EXAMPLE 1

Figure 18:
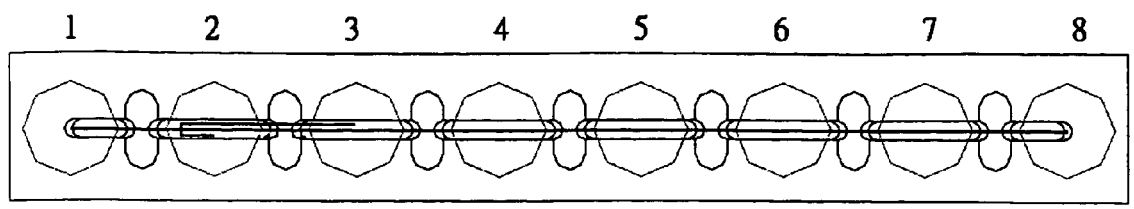
FIG. 18 illustrates a capillary electrophoresis chip in accordance with an embodiment of the present invention.

Device description. As illustrated in FIG. 18, a 1-sample CE chip is packaged into a package device 5. There are four inlet/outlets in CE chip 1. In FIG. 18, these inlet/outlets are located in reservoirs 1,2,3, and 8.

Buffer loading. About 30 µl of buffer is loaded into reservoir 8 of FIG. 18. Next, a syringe is used to force all of the channels in the CE chip 1 to become filled with buffer. Then, about 30 µl of buffer is loaded to reservoirs 1 and 3 of FIG. 18.

Sample loading and prerun. About 10 µl–20 µl of a liquid DNA sample (ΦX174 labeled by the fluorescence dye) is loaded into reservoir 2 of FIG. 18. An electrode 202 is placed in each reservoir. See, for example, FIG. 13. Then, the electrode potential configuration illustrated in FIG. 20 is used to prerun the separation channel.

Figure 19:
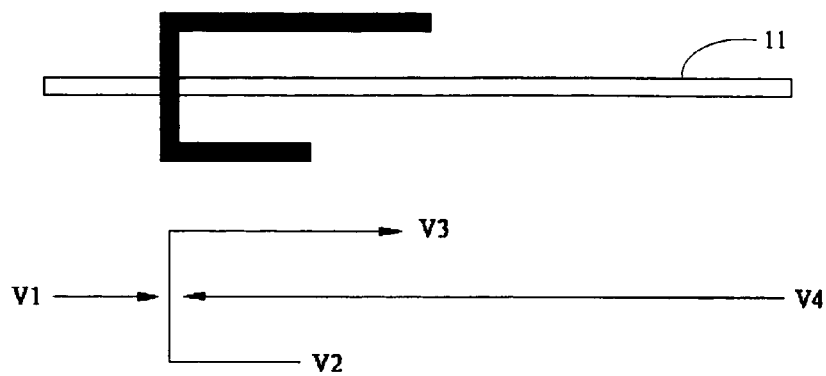
FIG. 19 illustrates an injection mode in accordance with an embodiment of the present invention.

Sample injection. The voltage setting is changed to injection mode. In injection mode, the electrode potential configuration is that of FIG. 19. Because of the difference in the electric potential between electrodes, the DNA sample will flow from the inlet of the reservoir 2 to the outlet of the waste reservoir 3, as illustrated in FIG. 19. The arrow direction in FIG. 19 describes the flow direction (from low voltage potential to high potential voltage).

Figure 20:
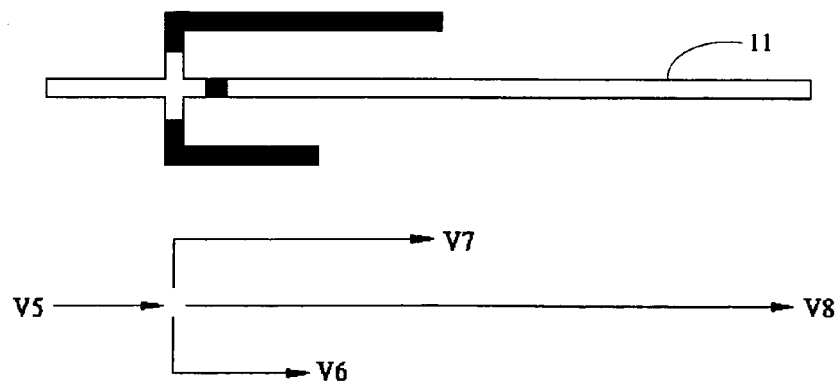
FIG. 20 illustrates a separation mode in accordance with an embodiment of the present invention.

Next, the voltage setting is changed to separation mode (the mode illustrated in FIG. 20). This causes one portion of the DNA sample to be injected into the main separation channel 11. Because of the DNA band size and the buffer, the DNA sample will start to separate in separation channel 11.

Figure 21:
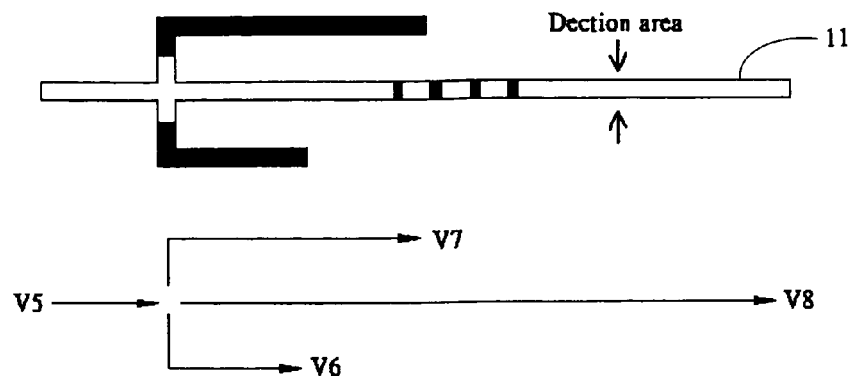
FIG. 21 illustrates a detection mode in accordance with an embodiment of the present invention.
Figure 22:
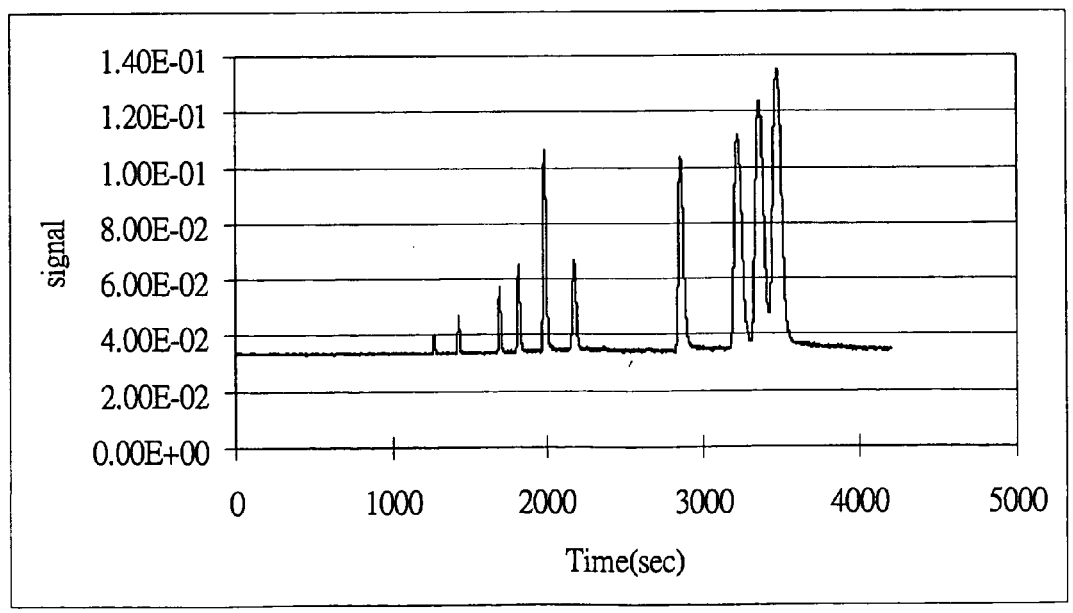
FIG. 22 illustrates a chromatograph of a Hae III enzymatic digest of ΦX174 after chromatic separation using a process in accordance with an embodiment of the present invention.

Sample detection. A mercury lamp or laser is used to excite the fluorescence dye and a PMT (photo multiplier tube) tube is used to observe the signal in the detection area (FIG. 21). FIG. 22 shows a resultant chromatograph for a Hae III enzymatic digest of ΦX174 that has been labeled by the fluorescence dye after chromatic separation using the above-described process. FIG. 22 shows that CE chip 1 effectively separates the products of the Hae III digest.

CONCLUSION

One skilled in the art will understand that the embodiment of the present invention as shown in the drawings and described above is exemplary only and not intended to be limiting. It will thus be seen that the objects of the present invention have been fully and effectively accomplished. Embodiments have been shown and described for the purposes of illustrating the functional and structural principles of the present invention and is subject to change without departure form such principles. Therefore, this invention includes all modifications encompassed within the spirit and scope of the following claims.

We claim:

1. A capillary electrophoresis device, comprising:
   a device body structure having a first surface and a second surface, wherein a plurality of reservoirs are arrayed on said first surface and a plurality of grooves are transversely defined on said second surface;
   at least one elongate capillary electrophoresis chip disposed in said device body structure, wherein each said at least one elongate capillary electrophoresis chip comprises:
   a substrate having a straight main separation channel and an injection channel;
   a coating layer that covers said substrate, and
   a plurality of access holes defined in said coating layer for allowing liquid communication between (i) said main separation channel and said injection channel, respectively, and (ii) reservoirs in said plurality of reservoirs that respectively correspond to said separation channel and said injection channel;
   wherein each said respective elongate capillary electrophoresis chip in said at least one elongate capillary electrophoresis chip is embedded into a corresponding groove such that the plurality of access holes in the respective elongate capillary chip are oriented towards corresponding reservoirs in said plurality of reservoirs; and means for applying and actively controlling a first set and a second set of electric potentials at each of said reservoirs in said plurality of reservoirs.

2. The capillary electrophoresis device of claim 1 wherein,
an elongate capillary electrophoresis chip in said at least one elongate capillary electrophoresis chip comprises one or more sample transport channels, and
said plurality of access hole include one or more access holes for respectively allowing liquid communication between said one or more sample transport channels and corresponding reservoirs in said plurality of reservoirs and wherein said first set of electric potentials is adapted to drive said sample from a transport channel in said one or more transport channels into said injection channel, and wherein said second set of electric potentials is adapted to drive a portion of said sample down said main separation channel.

3. The capillary electrophoresis device, as recited in claim 1, wherein said device body structure is an injection molding plastic structure.

4. The capillary electrophoresis device, as recited in claim 1, wherein a capillary electrophoresis chip in said at least one elongate capillary electrophoresis chip has a length/width ratio greater than 10.

5. The capillary electrophoresis device, as recited in claim 1, wherein said plurality of reservoirs are positioned with a well spacing that is consistent with an interval of a 384 well ELISA.

6. The capillary electrophoresis device, as recited in claim 1, wherein said coating layer comprises a dielectric thin film.

7. The capillary electrophoresis device, as recited in claim 6, wherein said dielectric thin film is silicon dioxide film, silicon nitride film, or a mixture thereof.

8. The capillary electrophoresis device, as recited in claim 1, wherein said substrate is made of glass.

9. A capillary electrophoresis device, comprising:
a device body structure (5) having a first surface (20) and a second surface (50), wherein a plurality of reservoirs (6) are arrayed on said first surface (20) and at least one groove (7) is transversely defined on said second surface (20);
wherein a groove (7) in said at least one groove is sufficiently deep that it is in communication with at least a portion of the plurality of reservoirs (6) and wherein said groove (7) includes a bonding agent receiving well (8);
an elongate capillary electrophoresis chip (1) disposed in said device body structure (5), wherein said elongate capillary electrophoresis chip (5) comprises:
a substrate (30) having a straight main separation channel (11) and an injection channel (2); and
a plurality of access holes (4) defined in said electrophoresis chip (1);
wherein said respective elongate capillary electrophoresis chip (1) is embedded into said groove (7) such that the plurality of access holes (4) are oriented towards corresponding reservoirs (6) in said plurality of reservoirs.

10. The capillary electrophoresis device of claim 9 wherein said groove (7) includes means for preventing bonding agent from entering into an access hole 4.

11. The capillary electrophoresis device of claim 9 wherein said groove (7) includes one or more steps (70) leading from said bonding agent receiving well (8) to a respective reservoir (6).

12. The capillary electrophoresis device of claim 9 wherein said groove includes one or more steps (70) leading from said respective reservoir (6) to said bonding agent receiving well (8).

* * * * *